US008017373B2

(12) United States Patent
Hill et al.

(10) Patent No.: US 8,017,373 B2
(45) Date of Patent: Sep. 13, 2011

(54) PROCESS FOR ENZYMATIC HYDROLYSIS OF PRETREATED LIGNOCELLULOSIC FEEDSTOCKS

(75) Inventors: Christopher Hill, Ottawa (CA); Brian Scott, Ottawa (CA); John Tomashek, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 687 days.

(21) Appl. No.: 11/846,653

(22) Filed: Aug. 29, 2007

(65) Prior Publication Data

US 2008/0057541 A1 Mar. 6, 2008

Related U.S. Application Data

(60) Provisional application No. 60/841,443, filed on Aug. 31, 2006.

(51) Int. Cl.
*C12N 9/42* (2006.01)

(52) U.S. Cl. .......................................... 435/209; 435/72

(58) Field of Classification Search ........................ None
See application file for complete search history.

(56) References Cited

U.S. PATENT DOCUMENTS

| | | | |
|---|---|---|---|
| 4,461,648 | A | 7/1984 | Foody |
| 5,763,254 | A | 6/1998 | Wöldike et al. |
| 5,866,407 | A | 2/1999 | Foody et al. |
| 6,015,703 | A | 1/2000 | White et al. |
| 2004/0053373 | A1 | 3/2004 | Foody et al. |
| 2004/0197890 | A1 | 10/2004 | Lange et al. |
| 2005/0277172 | A1 | 12/2005 | Day et al. |
| 2006/0008885 | A1 | 1/2006 | Wahnon et al. |
| 2006/0053514 | A1 | 3/2006 | Wu et al. |
| 2006/0057672 | A1 | 3/2006 | Bower et al. |

FOREIGN PATENT DOCUMENTS

| | | |
|---|---|---|
| WO | 02/24882 | 3/2002 |
| WO | 03/078644 | 9/2003 |

OTHER PUBLICATIONS

Juhasz et al., Applied Biochemistry and Biotechnology, 2004, vol. 113-116, p. 201-211.*
Itävaara et al., Journal of Environmental Polymer Degradation, 1999, vol. 7, No. 2, 1999.*
Zhang et al., Biotechnology and Bioengineering, 2004, vol. 88, No. 7, p. 797-824.*
Nidetzky et al., American Chemical Society, 1996, Chapter 8: Synergistic Interaction of cellulases from *Trichoderma reesei* during cellulose Degradation, in enzymatic Degradation of Insoluble Carbohydrates; Saddler et al., ASC Symposium Series; American Chemical Society, p. 90-112.*
Baker, et al., "Hydrolysis of Cellulose Using Ternary Mixtures of Purified Cellulases", Applied Biochemistry and Biotechnology, vol. 70-72 (1998) 395-403.

Barr, et al.,"Identification of Two Functionally Different Classes of Exocellulases", Biochemistry, vol. 35, No. 2 (1996) 586-92.
Boisset, et al., "Optimized Mixtures of Recombinant Humicola insolens Cellulases for the Biodegradation of Crystalline Cellulose", Biotechnology and Bioengineering, vol. 72, No. 3 (2001) 339-45.
Henrissat, et al., "Synergism of Cellulases from *Trichoderma reesei* in the Degradation of Cellulose", Biotechnology, vol. 3 (1985) 722-26.
Houghton, et al., "Breaking the Biological Barriers to Cellulosic Ethanol", U.S. Department of Energy Office of Science and Office of Energy Efficiency and Renewable Energy, Biofuels Joint Roadmap (2006) 3-4.
Irwin, et al., "Activity Studies of Eight Purified Cellulases: Specificity, Synergism and Binding Domain Effects", Biotechnology and Bioengineering, vol. 42, No. 8 (1993) 1002-13.
Jeoh, et al., "Effect of Cellulase Mole Fraction and Cellulose Recalcitrance on Synergism in Cellulose Hydrolysis and Binding", Biotechnol. Prog., vol. 22, No. 1 (2006) 270-77.
Kim, et al., "Factorial Optimization of a Six-cellulase Mixture", Biotechnology and Bioengineering, vol. 58, No. 5 (1998) 494-501.
Kubicek, "The Cellulase Proteins of Triochoderma reesei: Structure, Multiplicity, Mode of Action and Regulation of Formation", Advances in Biochemical Engineering/Biotechnology, vol. 45 (1992) 2-27.
Nidetzky, et al., "Cellulose hydrolysis by the cellulases from *Tichoderma reesei*: a new model for synergistic interaction", Biochem. J., vol. 298 (1994) 705-10.
Sheehan, et al., "Enzymes Energy, and the Environment: a Strategic Perspective on the U.S. Department of Energy's Research and Development Activities for Bioethanol", Biotechnology Progress, vol. 15, No. 5 (1999) 817-27.
Tolan, "Iogen's process for producing ethanol from cellulosic biomass", Clean Technologies and Environmental Policy, vol. 3 (2002) 339-45.
Väljamäe, et al., "Synergistic Cellulose Hydrolysis Can be Described in Terms of Fractal-Like Kinetics", Biotechnology and Bioengineering, vol. 82, No. 2 (2003) 254-57.
Walker, et al., "Engineering Cellulase Mixtures by Varying the Mole Fraction of Thermomonospora fusca E5 and E3, *Trichoderma reesei* CBH1 and Caldocellum saccharolyticum 11-glucosidase", Biotechnology and Bioengineering, vol. 42, No. 9 (1993) 1019-28.

(Continued)

*Primary Examiner* — Kade Ariani

(74) *Attorney, Agent, or Firm* — Fitzpatrick, Cella, Harper & Scinto

(57) ABSTRACT

An enzyme mixture for the enzymatic hydrolysis of a pretreated lignocellulosic feedstock to soluble sugars is provided. Also provided is a process for hydrolyzing a pretreated lignocellulosic feedstock with an enzyme mixture. The enzymatic hydrolysis comprises adding a cellulase enzyme mixture to a pretreated lignocellulosic feedstock. The cellulase enzyme mixture comprises a primary cellulase mixture of CBH1 and CBH2, and EG1 and EG2. The CBH1 and CBH2 being present at greater than or equal to 55% and less than 85% of the primary cellulase mixture. Furthermore, CBH2 is present at a fraction relative to CBH1 and CBH2, and EG2 is present at a fraction relative to the EG1 and EG2.

13 Claims, 8 Drawing Sheets

OTHER PUBLICATIONS

Wood, et al., "The Cellulase of *Tricohderma koningii*: Purification and Properties of Some Endoglucanase Components with Special Reference to Their Action on Cellulose When Acting Alone and in Synergism with the Cellobiohydrolase" Biochem. J., vol. 171 (1978) 61-72.

Wood, et al., "Synergism Between Enzymes Involved in the Solubilization of Native Cellulose", Advances in Chemistry Series, vol. 181 (1979) 181-209.

Wood, et al., "The mechanism of fungal cellulase action: Synergism between enzyme components of *Penicillium pinophilum* cellulase in solubilizing hydrogen bond-ordered cellulose", Biochem. J., vol. 260 (1989) 37-43.

Woodward, et al., "The role of cellulase concentration in determining the degree of synergism in the hydrolysis of microcrystalline cellulose", Biochem. J., vol. 255 (1988) 895-99.

Zhang, et al., "Substrate Heterogeneity Causes the Nonlinear Kinetics of Insoluble Cellulose Hydrolysis", Biotechnol. Bioeng., vol. 66, No. 1 (1999) 35-41.

Markov, et al., "New Effective Method for Analysis of the Component Compositions of Enzyme Complexes from *Trichoderma reesei*", Biochemistry (Moscow), vol. 70, No. 6 (2005) 657-63.

Zhang et al., "Toward an Aggregated Understanding of Enzymatic Hydrolysis of Cellulose: Noncomplexed Cellulase Systems", Biotechnology and Bioengineering, vol. 88, No. 7 (2004) 797-824.

* cited by examiner

PROCESS FOR ENZYMATIC HYDROLYSIS OF PRETREATED LIGNOCELLULOSIC FEEDSTOCKS

This application claims benefit of U.S. Provisional Application No. 60/841,443.

FIELD OF THE INVENTION

The present invention relates to an enzyme mixture. Also provided is a process for the enzymatic hydrolysis of a lignocellulosic feedstock, in particular for the enzymatic hydrolysis of a pretreated lignocellulosic feedstock.

BACKGROUND OF THE INVENTION

Fuel ethanol is currently produced from feedstocks such as corn starch, sugar cane, and sugar beets. However, the potential for production of ethanol from these sources is limited as most of the farmland which is suitable for the production of these crops is already in use to provide a food source for humans and animals. Furthermore, the production of ethanol from these feedstocks has significant greenhouse gas emissions because fossil fuels are used in the conversion process.

The production of ethanol from cellulose-containing feedstocks, such as agricultural residues, grasses, and forestry residues, has received much attention in recent years. The reasons for this are because these feedstocks are widely available and inexpensive and their use for ethanol production provides an alternative to burning or landfilling lignocellulosic waste materials. Moreover, a portion of the feedstock, lignin, can be used as a fuel to power the process, rather than fossil fuels. Several studies have concluded that, when the entire production and consumption cycle is taken into account, the use of ethanol produced from cellulose generates close to zero greenhouse gases.

The lignocellulosic feedstocks that are the most promising for ethanol production include (1) agricultural residues such as corn stover, wheat straw, barley straw, oat straw, rice straw, canola straw, and soybean stover; (2) grasses such as switch grass, miscanthus, cord grass, and reed canary grass; (3) fiber process residues such as corn fiber, beet pulp, pulp mill fines and rejects and sugar cane bagasse; (4) forestry wastes such as aspen wood, other hardwoods, softwood and sawdust; and (5) post-consumer waste paper products.

The most important process step of converting a lignocellulosic feedstock to ethanol involves converting the cellulose to glucose, for subsequent conversion to ethanol by fermentation. The two primary processes for accomplishing this are acid hydrolysis, which involves the hydrolysis of the feedstock using a single step of acid treatment, and enzymatic hydrolysis, which involves an acid pretreatment followed by hydrolysis with cellulase enzymes.

In the acid hydrolysis process, the feedstock is typically subjected to steam and sulfuric acid at a temperature, acid concentration and length of time that are sufficient to hydrolyze the cellulose to glucose and the hemicellulose to xylose and arabinose. The acid can be concentrated (25-80% w/w) or dilute (3-8% w/w). The glucose is then fermented to ethanol using yeast, and the ethanol is recovered and purified by distillation. Optionally, the glucose may be fermented to lactic acid, butanol, or other products.

In the enzymatic hydrolysis process, the reaction conditions are chosen such that the cellulose surface area is greatly increased as the fibrous feedstock is converted to a muddy texture, but there is little conversion of the cellulose to glucose. The pretreated cellulose is then hydrolyzed to glucose in a subsequent step that uses cellulase enzymes, and the steam and/or acid treatment in this case is known as pretreatment. The glucose may then be fermented to ethanol, lactic acid, butanol, or other products. Prior to the addition of enzyme, the pH of the acidic feedstock is adjusted to a value that is suitable for the enzymatic hydrolysis reaction. Typically, this involves the addition of alkali to a pH of between about 4 to about 6, which is the optimal pH range for many cellulases, although the pH can be higher if alkalophilic cellulases are used.

In one type of pretreatment process, the pressure produced by the steam is brought down rapidly with explosive decompression, which is known as steam explosion. Foody (U.S. Pat. No. 4,461,648) describes the equipment and conditions used in steam explosion pretreatment. Steam explosion with sulfuric acid carried out at a pH from 0.4 to 2.0 produces pretreated material that is uniform and requires less cellulase enzyme to hydrolyze cellulose than other pretreatment processes.

Cellulase enzymes catalyze the hydrolysis of the cellulose (hydrolysis of $\beta$-1,4-D-glucan linkages) in the feedstock into products such as glucose, cellobiose, and other cellooligosaccharides. Cellulase is a generic term denoting a multienzyme mixture comprising exo-acting cellobiohydrolases (CBHs), endoglucanases (EGs) and $\beta$-glucosidases ($\beta$G) that can be produced by a number of plants and microorganisms. The enzymes in the cellulase of *Trichoderma reesei* which contain a cellulose binding domain include CBH1 (more generally, Cel7A), CBH2 (Cel6A), EG1 (Cel7B), EG2 (Cel5), EG4 (Cel61A), EG5 (Cel45A), EG6 (Cel74A), Cip1, Cip2, acetyl xylan esterase, $\beta$-mannanase, and swollenin. EG3 (Cel12) is an example of a cellulolytic enzyme without a cellulose binding domain.

Cellulase enzymes work synergistically to hydrolyze cellulose to glucose. CBH1 and CBH2 act on opposing ends of cellulose chains to liberate cellobiose (Barr et al., 1996), while the endoglucanases act at internal locations in the cellulose. The primary product of these enzymes is cellobiose, which is further hydrolyzed to glucose by $\beta$-glucosidase. It is known that most CBHs and EGs bind to cellulose in the feedstock via carbohydrate-binding modules (CBMs), such as cellulose-binding domains (CBDs), while most $\beta$-glucosidase enzymes, including *Trichoderma* and *Aspergillus* $\beta$-glucosidase enzymes, do not contain such binding modules and thus remain in solution during hydrolysis. Cellulase enzymes may contain a linker region that connects the catalytic domain to the carbohydrate binding module. The linker region is believed to facilitate the activity of the catalytically active domain.

The kinetics of the enzymatic hydrolysis of insoluble cellulosic substrates by cellulases do not follow simple Michaelis-Menten behaviour (Zhang et al., 1999). Specifically, increasing the dosage of cellulase in a hydrolysis reaction does not provide a linearly dependent increase in the amount of glucose produced in a given time. There is also a significant decrease in the rate of reaction as cellulose hydrolysis proceeds (Tolan, 2002). Several explanations have been proposed to explain the decline in the reaction rate. The major hypotheses include product inhibition, increasing recalcitrance of substrate through the course of a hydrolysis and enzyme inactivation.

The kinetics of cellulase action make the enzymatic hydrolysis of pretreatment material an inefficient step in the production of cellulose ethanol. Reduction of the costs associated with enzymatic hydrolysis, through increasing cellulase production or activity, has been identified as a major opportunity for cost savings (Sheehan, 1999). A recent report from a cellulosic ethanol workshop sponsored by the United States Department of Energy estimated a 10- to 25-fold higher cost for producing the enzymes for cellulose ethanol than for the enzymes required to produce ethanol from starch (Houghton, 2006).

Several approaches have been taken to increase the activity of cellulase mixtures. Increasing the amount of β-glucosidase produced by the microorganism which also secretes the mixed cellulases alleviates product inhibition by cellobiose (U.S. Pat. No. 6,015,703). Rational design or random mutagenesis techniques can also be used to modulate the properties of individual enzymes, as demonstrated by the production of a CBH1 variant with increased thermostability (US2005/0277172). An alternate method to explore genetic diversity is to directly survey enzyme homologs from many cellulolytic species. This approach has been taken with CBH1 (US2004/0197890) and CBH2 (US2006/0053514). The construction of a fusion protein combining complementary activities from endo- and exo-cellulolytic enzymes has also been demonstrated (US2006/0057672). The modular domain structure of cellulolytic enzymes has permitted the construction of enzymes comprising the catalytic domain. The absence of a CBD has dramatic effects on the substrate binding and activities of these enzymes (US2004/0053373, US2006/0008885). Genetically engineered cellulose-hydrolyzing enzymes have been created that comprise novel combinations of the catalytically active domain, the linker region and the CBD (U.S. Pat. No. 5,763,254).

All of the approaches described above, while targeting different aspects of the enzymatic hydrolysis of cellulose, have not increased the cellulase activity sufficiently to overcome the high cost of cellulase for cellulose hydrolysis. One drawback of these strategies has been the focus on a single enzyme at a time, neglecting the synergies possible with other cellulolytic enzymes.

Therefore, a better approach to increasing the activity of a cellulase system is to focus on maximizing the activity of a mixture containing more than one cellulase component. It has been reported that the efficiency of cellulose hydrolysis by a combination of endo- and exo-cellulases is much greater than would be expected by summing the activities of these enzymes acting in isolation (Wood and McCrae, 1979). Previous studies have measured the synergy between the cellulolytic enzymes of *T. reesei* by observing the behaviour of binary or ternary mixtures (e.g. Nidetsky et al., 1994). For example, Wood et al. (1989) studied binary, tertiary and septenary blends of cellobiohydrolases and endoglucanases from *Penicillium pinophilum*. However, synergism was not observed in the binary blends of *Penicillium* enzymes. The synergism of binary combinations of three enzymes from the bacterium *Thermobifida fusca*, two of which are from the same families as those comprising the major *Trichoderma* enzymes, has also been characterized (Jeoh, 2006). However, improved performance has not been reported.

Several attempts have been made to develop a blend of CBHs and EGs to maximize the amount of cellulose hydrolysis for a given enzyme dosage (the enzyme dosage is the mass of enzyme required to hydrolyse a given mass of cellulose). For example, optimized blends of cellulases of mixed origin including bacteria, largely derived from *T. fusca*, have been reported (Irwin, 1993; Walker et al., 1993; Kim et al., 1998). *Trichoderma* CBH1 and CBH2 were included in these studies, but bacteria are unable to produce family 7 cellulases and EG1 was therefore not part of these blends. Baker et al. (1998) attempted to determine an optimal blend of *Trichoderma* CBH1, CBH2, and EG1, but did not include EG2 in their experiment. In the case of Baker et al., the substrate was Sigmacell, a microcrystalline cellulose preparation. Boisset et al. (2001) performed an optimization of a ternary blend of CBH1, CBH2 and EG5 derived from *Humicola insolens* on the substrate of bacterial cellulose. However, these studies have not succeeded in developing cellulase enzyme mixtures with improved performance for the hydrolysis of cellulose within pretreated lignocellulosic biomass.

Thus, in spite of much research effort, there remains a need for an improved cellulase enzyme mixture for the hydrolysis of cellulose in a pretreated lignocellulosic feedstock. The absence of such an enzyme mixture represents a large hurdle in the commercialization of cellulose conversion to soluble sugars including glucose for the production of ethanol and other products.

SUMMARY OF INVENTION

The present invention relates to an enzyme mixture. Also provided is a process for the enzymatic hydrolysis of a lignocellulosic feedstock, in particular for the enzymatic hydrolysis of a pretreated lignocellulosic feedstock.

It is an object of the invention to provide a process for an improved enzymatic hydrolysis of a pretreated lignocellulosic feedstock.

In particular, the present invention provides for the enhanced conversion of a pretreated lignocellulosic feedstock to soluble sugars utilizing a group of combinations of the four primary cellulase enzymes, CBH1, CBH1, EG1 and EG2.

According to one aspect of the invention, there is provided a process for the enzymatic hydrolysis of a pretreated lignocellulosic feedstock to soluble sugars, the enzymatic hydrolysis comprising addition of a cellulase enzyme mixture to the pretreated lignocellulosic feedstock, the cellulase enzyme mixture comprising a primary cellulase mixture of CBH1 and CBH2 cellobiohydrolases and EG1 and EG2 endoglucanases, the CBH1 and CBH2 cellobiohydrolases being present at greater than or equal to 55% and less than 85% of the primary cellulase mixture and the CBH2 being present at a fraction relative to CBH1 and CBH2 cellobiohydrolases as defined by $f_{C2}$ and the EG2 being present at a fraction relative to the EG1 and EG2 endoglucanases as defined by $f_{E2}$, wherein when the CBH1 and CBH2 cellobiohydrolases are present at greater than or equal to 55% and less than 65% of the primary cellulases, the $f_{C2}$ and the $f_{E2}$ are at values included within Zone 1 of FIG. 3A;

when the CBH1 and CBH2 cellobiohydrolases are present at greater than or equal to 65% and less than 75% of the primary cellulases, the $f_{C2}$ and the $f_{E2}$ are at values included within Zones 1, 2, and 3 of FIG. 3B; and when the CBH1 and CBH2 cellobiohydrolases are present at greater than or equal to 75% and less than 85% of the primary cellulases, the $f_{C2}$ and the $f_{E2}$ are at values included within Zones 1, 2 and 3 of FIG. 3C.

According to another aspect of the invention there is provided a cellulase enzyme mixture as defined above.

Preferably, the CBH1 and CBH2 cellobiohydrolases are present at greater than or equal to 65% and less than 85% of the primary cellulases. When said CBH1 and CBH2 cellobiohydrolases are present at 65% to 75% of the primary cellulases, the $f_{C2}$ and said $f_{E2}$ are each preferably at values included within Zones 2 and 3 of FIG. 3B. Preferably, the $f_{C2}$ and the $f_{E2}$ are each at values included within Zone 3 of FIG. 3B. When the CBH1 and CBH2 cellobiohydrolases are present at 75% to 85% of the primary cellulases, the $f_{C2}$ and $f_{E2}$ are preferably at values included within Zones 2 and 3 of FIG. 3C. Preferably, the $f_{C2}$ and $f_{E2}$ are each at values included within Zone 3 of FIG. 3C.

The present invention also pertains to any of the aforementioned aspects of the invention as defined above, wherein the primary cellulases are from a fungal source. The primary cellulase coding sequences may be from an *Ascomycete* or *Basidiomycete*. Preferably, the primary cellulases are from *Trichoderma* ssp, *Aspergillus* ssp, *Hypocrea* ssp or *Humicola* ssp. More preferably, the primary cellulase coding sequences are from *Trichoderma reesei*.

The present invention also pertains to any of the aforementioned aspects of the invention as defined above, wherein the primary cellulases are obtained from an organism by expressing coding sequences which are endogenous to said organism. Alternatively, the primary cellulases are obtained from an organism by expressing coding sequences which are heterologous to said organism. Preferably, the primary cellulases are from *Trichoderma reesei*.

Preferably, the enzymatic hydrolysis converts at least about 80% of the cellulose in the pretreated lignocellulosic feedstock to soluble sugars. The soluble sugars may be fermented to produce ethanol, lactic acid, butanol, or a combination thereof.

The enzymatic hydrolysis is preferably carried out with cellulase enzymes comprising β-glucosidase and a secretome of *Trichoderma reesei*.

The primary cellulase mixtures encompassed by the invention display significantly higher activity than those described in the prior art. The results show that the cellulase mixtures of the present invention are from about 10% to about 50%, or any amount therebetween, about 10% to about 25%, or any amount therebetween, or from about 10% to about 15%, or any amount therebetween, more potent or more active than currently available cellulase blends.

The economic feasibility of cellulose-to-ethanol technology has been limited by the cost of cellulase enzymes. By providing for enzymes with improved activity, the cellulase enzymes of the present invention increases the economy of the process and represent a significant advance over the prior art.

This summary of the invention does not necessarily describe all features of the invention.

BRIEF DESCRIPTION OF THE DRAWINGS

FIG. 3 shows plots of the enzyme activities of primary cellulase mixtures containing CBH1, CBH2, EG1 and EG2. The activities of various cellulase mixtures are plotted as measured at various fractional contents of EG2 relative to the total EG amount and CBH2 relative to the total CBH content (depicted as $f_{E2}$ and $f_{C2}$, respectively). The value listed within each square indicates the activity of the mixture compared to a benchmark value as described in the examples. Activities of the various cellulase mixtures are expressed relative to the activities of a Benchmark Blend (CBH1, CBH2, EG1, EG2, at 57%, 29%, 7%, 7%, wt %).

FIG. 4A shows blends comprising Zone 1 of FIG. 3A and Zone 1, 2 and 3 regions from FIGS. 3B and 3C. FIG. 4B shows blends comprising Zone 2 and 3 regions from FIGS. 3B and 3C. FIG. 4C shows blends comprising Zone 3 regions from FIGS. 3B and 3C.

DETAILED DESCRIPTION OF THE INVENTION

Figure 1:
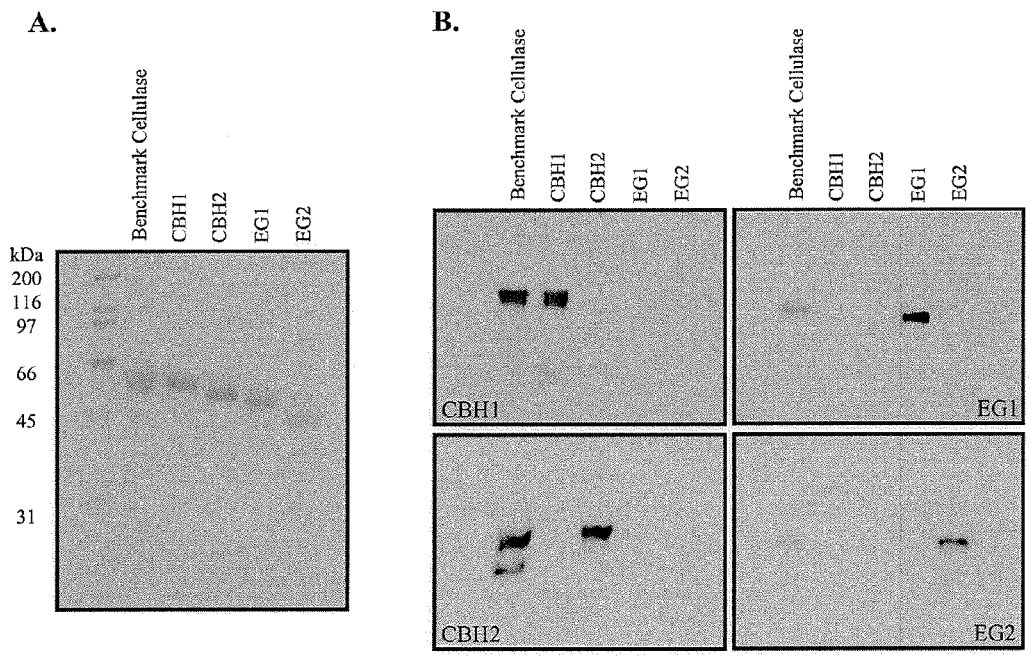
FIG. 1 contains the SDS-PAGE and Western blot analysis of the purified primary cellulase components. A Coomassie Blue stain of purified CBH1, CBH2, EG1 and EG2 after SDS-PAGE is shown in panel A. A *Trichoderma* cellulase was analyzed in parallel for comparison. Component-specific Western blots of these samples were performed following SDS-PAGE separation and electro-transfer to a PVDF membrane (panel B).

The present invention relates to an enzyme mixture. Also provided is a process for the enzymatic hydrolysis of a lignocellulosic feedstock, in particular for the enzymatic hydrolysis of a pretreated lignocellulosic feedstock.

The following description is of preferred embodiments.

The present invention relates to a cellulase enzyme mixture comprising primary cellulases to be used for hydrolyzing a pretreated lignocellulosic feedstock. "Primary cellulase enzymes" or "primary cellulases" are defined as the cellobiohydrolases, CBH1 and CBH2, and the endoglucanases, EG1 and EG2. In addition to the primary cellulases, CBH1, CBH2, EG1 and EG2, the cellulase enzyme mixture may comprise additional cellulases as well as β-glucosidase enzyme components as described in further detail below.

The following definitions refer to classification of cellobiohydrolases, endoglucanases and β-glucosidases as defined by the by the Joint Commission on Biochemical Nomenclature of the International Union of Biochemistry and Molecular Biology (Published in *Enzyme Nomenclature* 1992, Academic Press, San Diego, Calif., ISBN 0-12-227164-5; with suppliments in *Eur. J. Biochem*. 1994, 223, 1-5; *Eur. J. Biochem*. 1995, 232, 1-6; *Eur. J. Biochem*. 1996, 237, 1-5; *Eur. J. Biochem*. 1997, 250; 1-6, and *Eur. J. Biochem*. 1999, 264, 610-650, each of which are incorporated herein by reference; also see: chem.qmul.ac.uk/iubmb/enzyme/) and to the glycohydrolase families of cellulases and β-glucosidases as defined by the CAZy system which is accepted as a standard nomenclature for glycohydrolase enzymes (Coutinho, P. M. & Henrissat, B., 1999, "Carbohydrate-active enzymes: an integrated database approach." In *Recent Advances in Carbohydrate Bioengineering*, H. J. Gilbert, G. Davies, B. Henrissat and B. Svensson eds., The Royal Society of Chemistry, Cambridge, pp. 3-12, which is incorporated herein by reference; also see: afmb.cnrs-mrs.fr/CAZY/) and is familiar to those skilled in the art.

"CBH1" is a carbohydrate active enzyme expressed from a DNA sequence coding for a glycohydrolase (GH) Family 7 catalytic domain classified under EC 3.2.1.91. Any carbohydrate active enzyme with a 60% to 100% amino acid sequence identity to any CBH1 enzyme or more preferably 65% to 100% amino acid sequence identity and that exhibits CBH1 activity as known to one of skill in the art (see references for cellobiohydrolase nomenclature), is similarly defined as a CBH1. For example, the CBH1 may be any carbohydrate active enzyme with 60, 65, 70, 75, 80, 85, 90, 95 or 100% amino acid sequence identity to any CBH1 enzyme and that exhibits CBH1 activity as known to one of skill in the art. Preferably, the CBH1 is functionally linked to a carbohydrate binding module (CBM) with a high affinity for crystalline cellulose, such as a Family 1 cellulose binding domain.

Sequence identify can be readily determined by alignment of the amino acids of the two sequences, either using manual alignment, or any sequence alignment algorithm as known into one of skill in the art, for example but not limited to, BLAST algorithm (BLAST and BLAST 2.0; Altschul et al., Nuc. Acids Res. 25:3389-3402, 1977; and Altschul et al., J. Mol. Biol. 215:403-410, 1990), the algorithm disclosed by Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

"CBH2" is defined as a carbohydrate active enzyme expressed from a DNA sequenced coding for a glycohydrolase (GH) Family 6 catalytic domain classified under EC 3.2.1.91. Any carbohydrate active enzyme with 60% to 100% amino acid sequence identity to any CBH2 enzyme, or more preferably 65% to 100% amino acid sequence identity and that exhibits CBH2 activity as known to one of skill in the art (see references for cellobiohydrolase nomenclature), is similarly defined as a CBH2. For example, the CBH2 may be any carbohydrate active enzyme with 60, 65, 70, 75, 80, 85, 90, 95 or 100% amino acid sequence identity to any CBH2 enzyme and that exhibits CBH2 activity as known to one of skill in the art. Preferably, the CBH2 is functionally linked to a carbohydrate binding module (CBM) with a high affinity for crystalline cellulase, such as a Family 1 cellulose binding domain. Sequence identity can be determined as outlined above.

"EG1" is defined as a carbohydrate active enzyme expressed from a DNA sequenced coding for a glycohydrolase (GH) Family 7 catalytic domain classified under EC 3.2.1.4. Any carbohydrate active enzyme with 60% to 100%, or more preferably 65% to 100% amino acid sequence identity to any EG1 enzyme and that exhibits EG1 activity as known to one of skill in the art (see references for endoglucanase nomenclature), is similarly defined as an EG1. For example, the EG1 may be any carbohydrate active enzyme with 60, 65, 70, 75, 80, 85, 90, 95 or 100% amino acid sequence identity to any EG1 enzyme and that exhibits EG1 activity as known to one of skill in the art. Preferably, the EG1 is functionally linked to a carbohydrate binding module (CBM) with a high affinity for crystalline cellulase, such as a Family 1 cellulose binding domain. Sequence identity can be determined as outlined above.

"EG2" is defined as a carbohydrate active enzyme expressed from a DNA sequenced coding for a glycohydrolase (GH) Family 5 catalytic domain classified under EC 3.2.1.4. Any carbohydrate active enzyme with 60% to 100% amino acid sequence identity, or more preferably 65% to 100% amino acid sequence identity to any EG2 enzyme and that exhibits EG2 activity as known to one of skill in the art (see references for endoglucanase nomenclature), is similarly defined as an EG2. For example, the EG2 may be any carbohydrate active enzyme with 60, 65, 70, 75, 80, 85, 90, 95 or 100% amino acid sequence identity to any EG2 enzyme and that exhibits EG2 activity as known to one of skill in the art. Preferably, the EG2 is functionally linked to a carbohydrate binding module (CBM) with a high affinity for crystalline cellulase, such as a Family 1 cellulose binding domain. Sequence identity can be determined as outlined above.

"β-Glucosidase" is defined as any enzyme from the GH family 3 that is also classified under EC 3.2.1.21. BGL1 is defined as the enzyme expressed from the bgl1 gene of *Trichoderma reesei*. Any protein sequence with 60% to 100% amino acid sequence identity to BGL1 enzyme or more preferably 65% to 100% amino acid sequence identity and that exhibits β-glucosidase activity as known to one of skill in the art (see references for endoglucanase nomenclature), is similarly defined as a BGL1. For example, the BGL1 may be any carbohydrate active enzyme with 60, 65, 70, 75, 80, 85, 90, 95 or 100% amino acid sequence identity to any BGL1 enzyme and that exhibits BGL1 activity as known to one of skill in the art. Sequence identity can be determined as outlined above.

The cellobiohydrolases CBH1 and CBH2 within the cellulase enzyme mixture of the present invention (i.e., the combined content of CBH1 and CBH2) are present at greater than or equal to 55% and less than 85% of the primary cellulase mixture, within the cellulase mixture (that is, the amounts of CBH1 and CBH2 comprise from about 55% to about 85% of the primary cellulase mixture, of the cellulase enzyme mixture). Within this range of mixtures of CBH1 and CBH2, three sets of mixtures of these primary cellulase enzymes, dependent on the different fractions of the combined CBH1 and CBH2 content relative to the primary cellulases (depicted as the % CBH in FIGS. 3A, 3B and 3C), have been identified as exhibiting an advantage in carrying out hydrolysis of a lignocellulosic feedstock. These sets of mixtures may be defined by the CBH2 fraction relative to CBH1 and CBH2 cellobiohydrolases (on an amount, wt, or wt:vol basis), where this fraction is referred to as $f_{C2}$:

$$f_{C2} = CBH2/(CBH1+CBH2).$$

The EG2 fraction relative to the EG1 and EG2 endoglucanases is referred to as $f_{E2}$:

$$f_{E2} = EG2/(EG1+EG2).$$

Figure 3A:
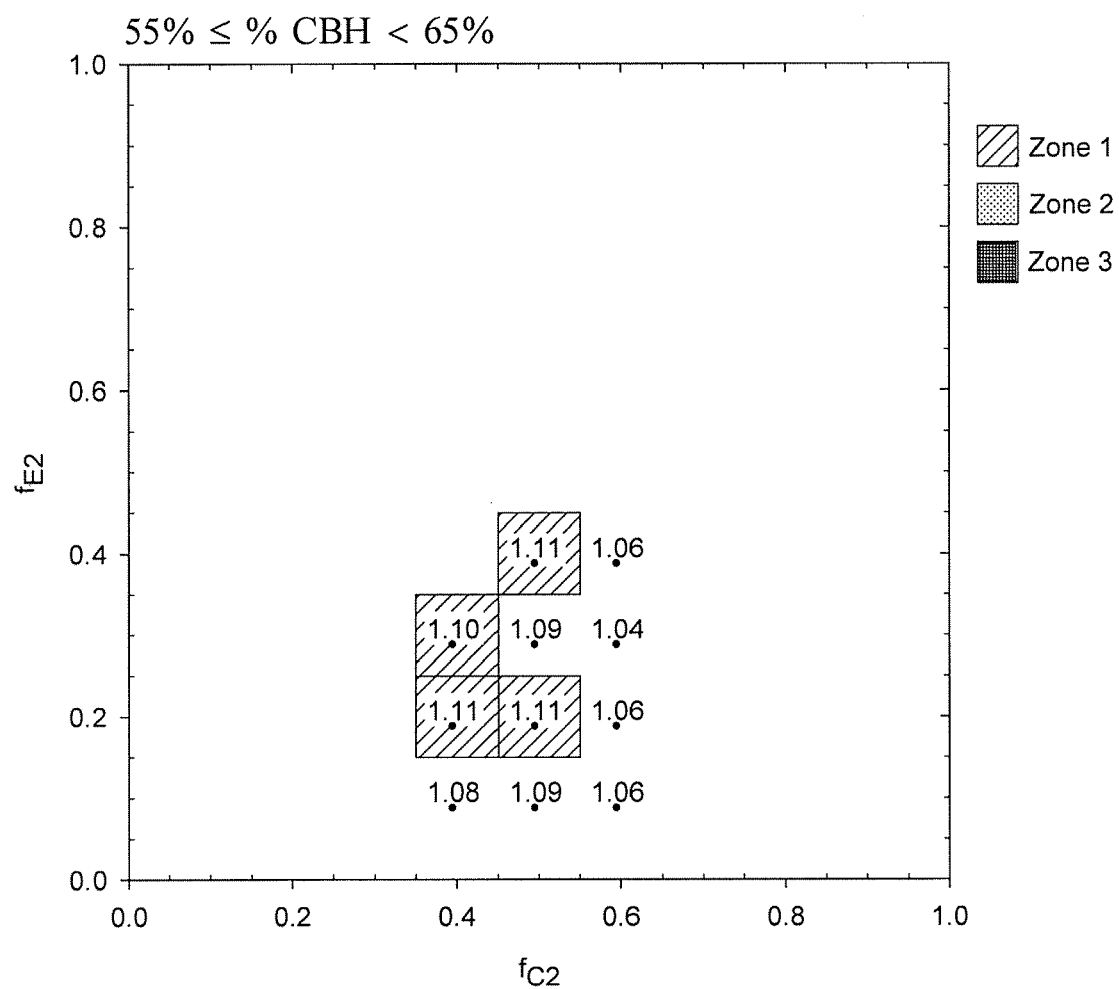
FIG. 3A shows the activities of mixtures in which the combined CBH1 and CBH2 content is greater than or equal to 55% and less than 65% of the total primary cellulases.
Figure 3B:
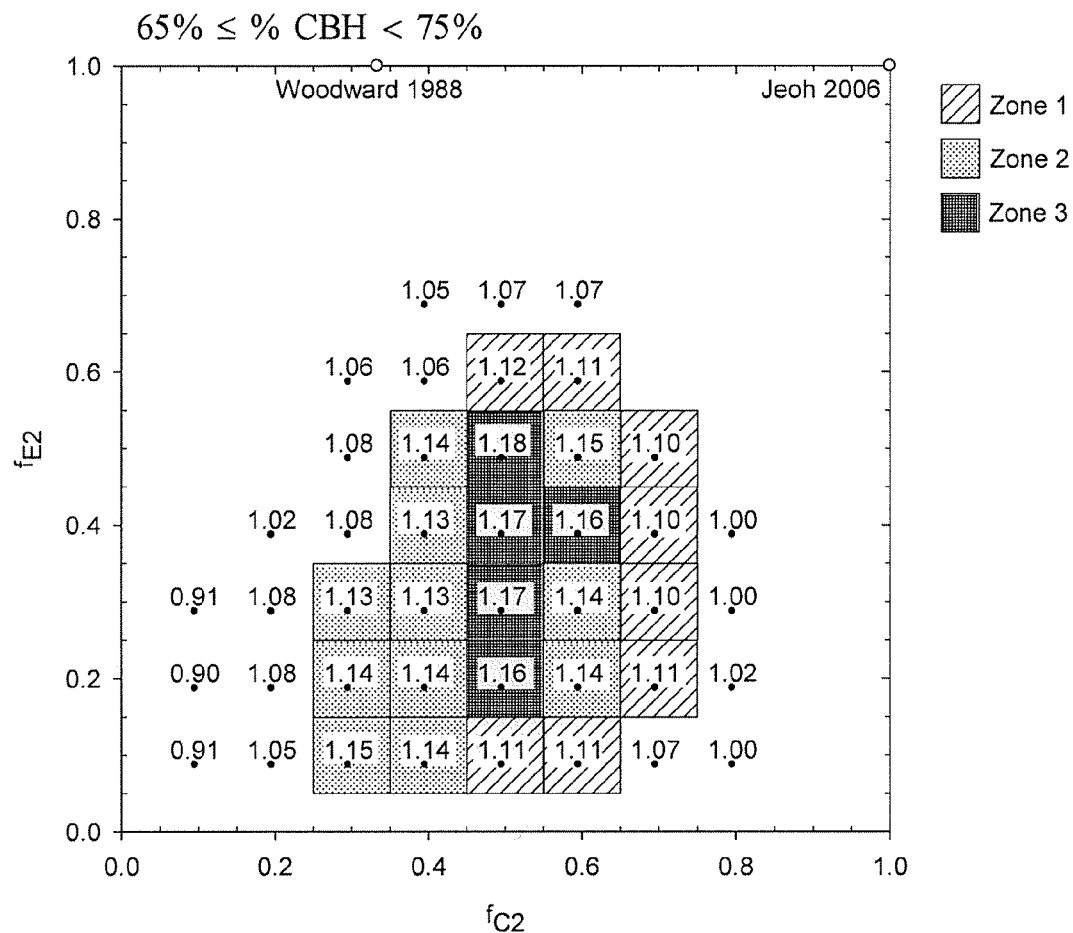
FIG. 3B shows the activities of mixtures in which the combined CBH1 and CBH2 content is greater than or equal to 65% and less than 75% of the total primary cellulases.
Figure 3C:
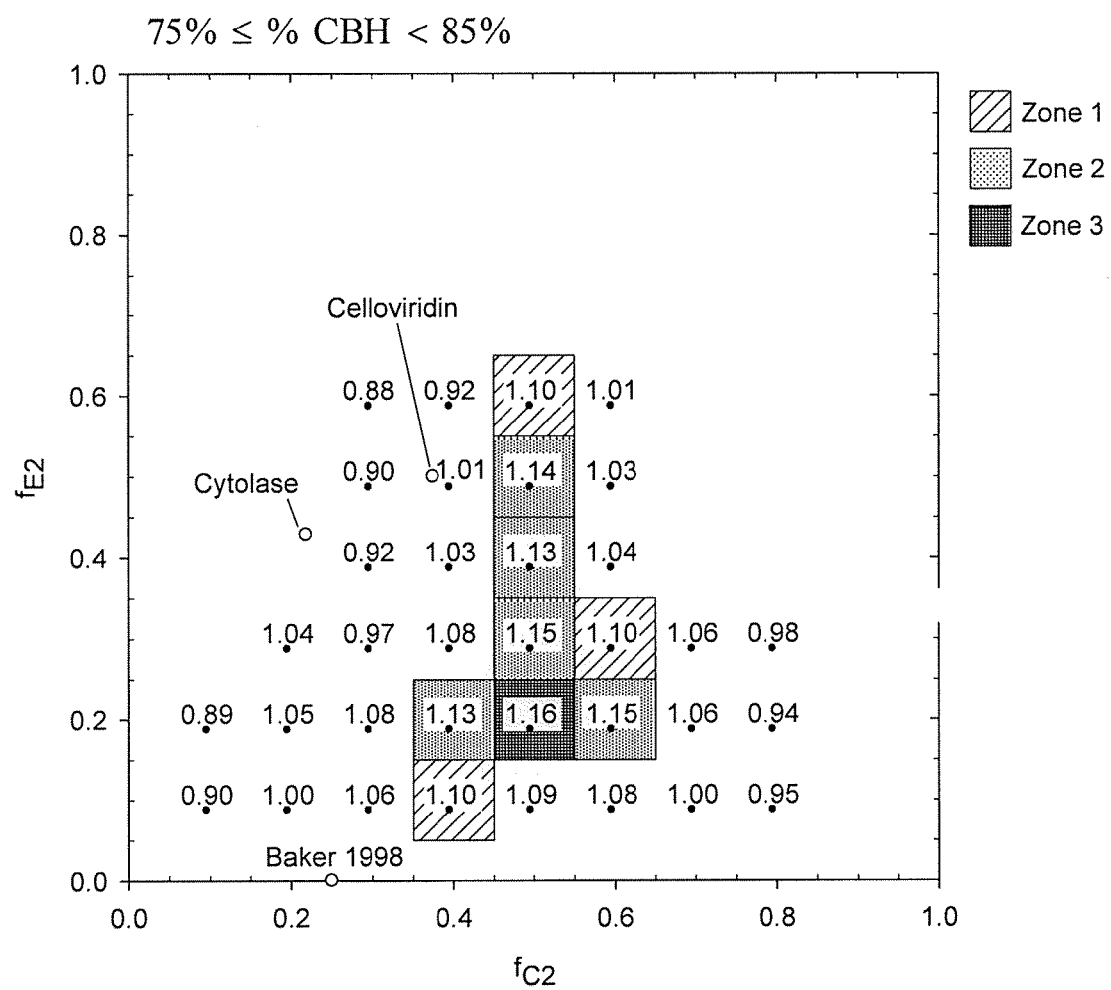
FIG. 3C shows the activities of mixtures in which the combined CBH1 and CBH2 content is greater than or equal to 75% and less than 85% of the total primary cellulases.
Figure 4:
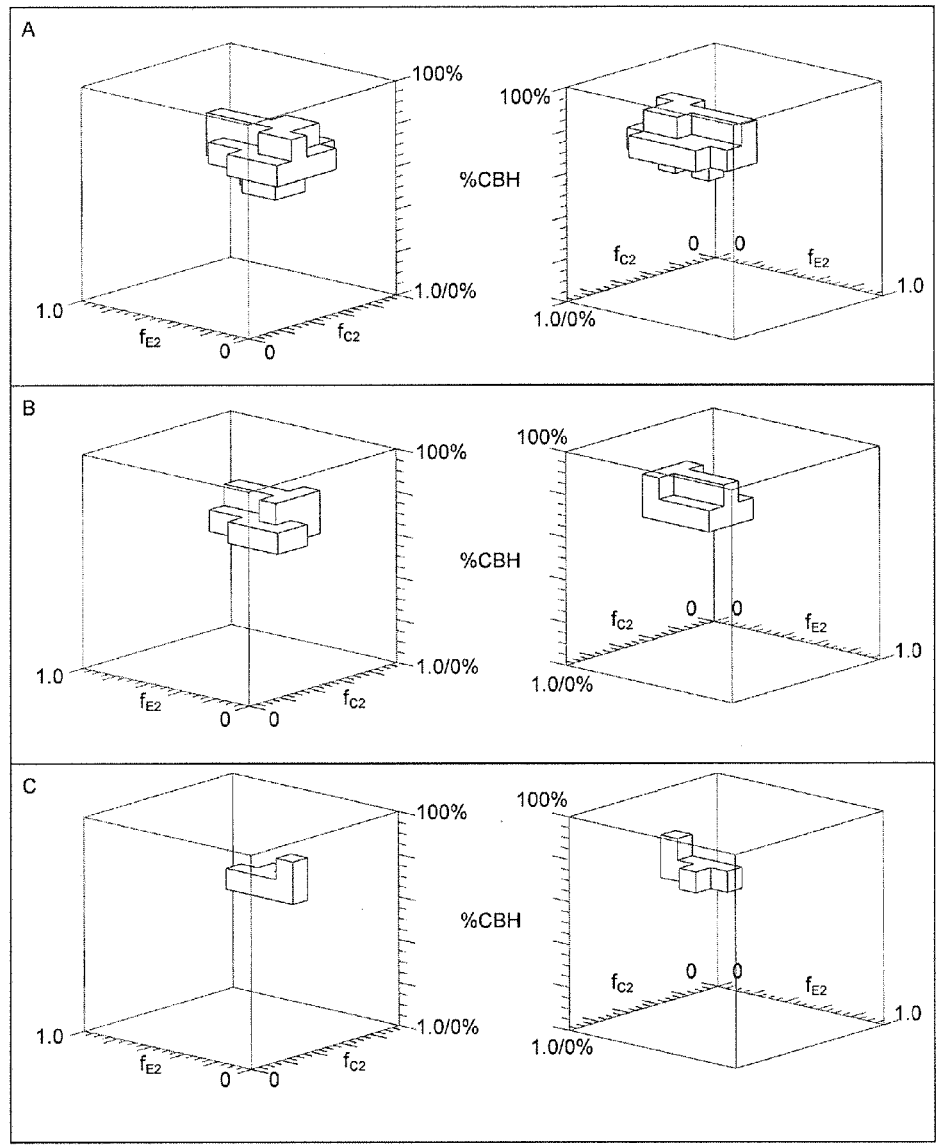
FIG. 4 is a three dimensional plot showing the regions occupied by improved blends of primary cellulases in the blend space defined by % CBH, $f_{C2}$ and $f_{E2}$. Activities are relative to the Benchmark Blend. Each pair of images provides two views of the same region and differ in a rotation of 180° around the % CBH axis.

The component blend for the first, second and third mixtures are mapped onto FIGS. 3A, 3B and 3C, respectively. The three dimensional representations of the component blend space described by these mixtures are shown in FIG. 4.

CBH1 and CBH2 Comprising from about 55% to about 65% of the Primary Cellulase Mixture When the CBH1 and CBH2 cellobiohydrolases are present at greater than or equal to 55% and less than 65% of the primary cellulases, the fraction of cellobiohydrolases that is CBH2 ($f_{C2}$) and the fraction of endoglucanases that is EG2 ($f_{E2}$) is covered by Zone 1 of FIG. 3A. Zone 1 of FIG. 3A includes the following three regions:

$f_{C2}$ values greater than or equal to 0.35 and less than 0.45 and $f_{E2}$ values greater than or equal to 0.15 and less than 0.35;

$f_{C2}$ values greater than or equal to 0.45 and less than 0.55 and $f_{E2}$ values greater than or equal to 0.15 and less than 0.25; and $f_{C2}$ values greater than or equal to 0.45 and less than 0.55 and $f_{E2}$ values greater than or equal to 0.35 and less than 0.45.

CBH1 and CBH2 Comprising from about 65% to about 75% of the Primary Cellulase Mixture When the CBH1 and CBH2 cellobiohydrolases are present at greater than or equal to 65% and less than 75% of the primary cellulases, the $f_{C2}$ and the $f_{E2}$ are at values included within Zones 1, 2, and 3 of FIG. 3B. Zones 1, 2 and 3 include the following regions:

$f_{C2}$ values greater than or equal to 0.25 and less than 0.35 and $f_{E2}$ values greater than or equal to 0.05 and less than 0.35;
$f_{C2}$ values greater than or equal to 0.35 and less than 0.45 and $f_{E2}$ values greater than or equal to 0.05 and less than 0.55;
$f_{C2}$ values greater than or equal to 0.45 and less than 0.65 and $f_{E2}$ values greater than or equal to 0.05 and less than 0.65; and
$f_{C2}$ values greater than or equal to 0.65 and less than 0.75 and $f_{E2}$ values greater than or equal to 0.15 and less than 0.55.

Zones 2 and 3 of FIG. 3B includes the following regions:
$f_{C2}$ values greater than or equal to 0.25 and less than 0.35 and $f_{E2}$ values are greater than or equal to 0.05 and less than 0.35;
$f_{C2}$ values greater than or equal to 0.35 and less than 0.45 and $f_{E2}$ values are greater than or equal to 0.05 and less than 0.55; and
$f_{C2}$ values greater than or equal to 0.45 and less than 0.65 and $f_{E2}$ values greater than or equal to 0.15 and less than 0.55.

Zone 3 of FIG. 3B includes the following two regions:
$f_{C2}$ values greater than or equal to 0.45 and less than 0.55 and $f_{E2}$ values greater than or equal to 0.15 and less than 0.55; and
$f_{C2}$ values greater than or equal to 0.55 and less than 0.65 and $f_{E2}$ values greater than or equal to 0.35 and less than 0.45.

Preferably, the $f_{C2}$ and the $f_{E2}$ include values within Zones 2 and 3 of FIG. 3B. More preferably, the $f_{C2}$ and the $f_{E2}$ include values within Zone 3 of FIG. 3B.

CBH1 and CBH2 Comprising from about 75% to about 85% of the Primary Cellulase Mixture When the CBH1 and CBH2 cellobiohydrolases are present at less than or equal to 75% and less than 85% of the primary cellulases, the $f_{C2}$ and the $f_{E2}$ are at values included within Zones 1, 2 and 3 of FIG. 3C. Zones 1, 2 and 3 include the following regions:

$f_{C2}$ values greater than or equal to 0.35 and less than 0.45 and $f_{E2}$ values greater than or equal to 0.05 and less than 0.25;
$f_{C2}$ values greater than or equal to 0.45 and less than 0.55 and $f_{E2}$ values greater than or equal to 0.15 and less than 0.65; and
$f_{C2}$ values greater than or equal to 0.55 and less than 0.65 and $f_{E2}$ values greater than or equal to 0.15 and less than 0.35.

Zones 2 and 3 include the following three regions:
$f_{C2}$ values greater than or equal to 0.35 and less than 0.45 and $f_{E2}$ values greater than or equal to 0.15 and less than 0.25;
$f_{C2}$ values greater than or equal to 0.45 and less than 0.55 and $f_{E2}$ values greater than or equal to 0.15 and less than 0.55; and
$f_{C2}$ values greater than or equal to 0.55 and less than 0.65 and $f_{E2}$ values greater than or equal to 0.15 and less than 0.25.

Zone 3 defines a single region including $f_{C2}$ values between 0.45 and 0.55 and $f_{E2}$ values between 0.15 and 0.25.

Preferably, the $f_{C2}$ and the $f_{E2}$ include values within Zones 2 and 3 of FIG. 3C. Most preferably, the $f_{C2}$ and the $f_{E2}$ include values within Zone 3 of FIG. 3C.

The fraction or percentage of each cellulase component within the cellulase mixture is determined by using the methods of Example 3.

Therefore, the present invention provides an enzyme mixture and a process for the enzymatic hydrolysis of a pretreated lignocellulosic feedstock to soluble sugars comprising hydrolyzing the pretreated feedstock with the enzyme mixture. The cellulase enzyme mixture comprises a primary cellulase mixture of CBH1 and CBH2 cellobiohydrolases and EG1 and EG2 endoglucanases. The CBH1 and CBH2 cellobiohydrolases are present at a combined content greater than or equal to 55% and less than 85% of the primary cellulase mixture. The CBH2 are present at a fraction, defined by $f_{C2}$, relative to CBH1 and CBH2 cellobiohydrolases, and the EG2 are present at a fraction, defined by $f_{E2}$, relative to the EG1 and EG2 endoglucanases, wherein (i) when said CBH1 and CBH2 cellobiohydrolases are present at greater than or equal to 55% and less than 65% of the primary cellulases, said $f_{C2}$ and said $f_{E2}$ are at values included within Zones 1 of FIG. 3A;

(ii) when said CBH1 and CBH2 cellobiohydrolases are present at greater than or equal to 65% and less than 75% of the primary cellulases, said $f_{C2}$ and said $f_{E2}$ are at values included within Zones 1, 2, and 3 of FIG. 3B; and (iii) when said CBH1 and CBH2 cellobiohydrolases are present at greater than or equal to 75% and less than 85% of the primary cellulases, said $f_{C2}$ and said $f_{E2}$ are at values included within Zones 1, 2, and 3 of FIG. 3C.

The cellulase enzyme mixture of the invention is used for the enzymatic hydrolysis of a "pretreated lignocellulosic feedstock." A pretreated lignocellulosic feedstock is a material of plant origin that, prior to pretreatment, contains at least 20% cellulose (dry wt) and at least 12% lignin (dry wt), and that has been subjected to physical and/or chemical processes to make the fiber more accessible and/or receptive to the actions of cellulolytic enzymes.

After pretreatment, the lignocellulosic feedstock may contain greater than about 20% cellulose and greater than about 12% lignin. In one embodiment, the pretreated lignocellulosic feedstock contains greater than about 20% cellulose and greater than about 10% lignin.

Lignocellulosic feedstocks that may be used in the invention include, but are not limited to, agricultural residues such as corn stover, wheat straw, barley straw, rice straw, oat straw, canola straw, and soybean stover; fiber process residues such as corn fiber, sugar beet pulp, pulp mill fines and rejects or sugar cane bagasse; forestry residues such as aspen wood, other hardwoods, softwood, and sawdust; or grasses such as switch grass, miscanthus, cord grass, and reed canary grass.

The lignocellulosic feedstock may be first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, a hammer mill.

Non-limiting examples of pretreatment processes include chemical treatment of a lignocellulosic feedstock with sulfuric or sulfurous acid, or other acids; ammonia, lime, ammonium hydroxide, or other bases; ethanol, butanol, or other organic solvents; or pressurized water (See U.S. Pat. Nos. 4,461,648, 5,916,780, 6,090,595, 6,043,392, 4,600,590, Weil et al. (1997) and Öhgren, K., et al. (2005); which are incorporated herein by reference).

The pretreatment may be carried out to hydrolyze the hemicellulose, or a portion thereof, that is present in the lignocellulosic feedstock to monomeric sugars, for example xylose, arabinose, mannose, galactose, or a combination thereof. Preferably, the pretreatment is carried out so that nearly complete hydrolysis of the hemicellulose and a small amount of conversion of cellulose to glucose occurs. During the pretreatment, typically an acid concentration in the aqueous slurry from about 0.02% (w/w) to about 2% (w/w), or any amount therebetween, is used for the treatment of the lignocellulosic feedstock. Preferably, the acid used during pretreatment is sulfuric acid.

The pretreated lignocellulosic feedstock may be processed after pretreatment but prior to the enzymatic hydrolysis by any of several steps, such as dilution with water, washing with water, buffering, filtration, or centrifugation, or a combination of these processes, as is familiar to those skilled in the art.

The pretreated lignocellulosic feedstock is next subjected to enzymatic hydrolysis. By the term "enzymatic hydrolysis", it is meant a process by which cellulase enzymes act on cellulose to convert all or a portion thereof to soluble sugars. Soluble sugars are meant to include water-soluble hexose monomers and oligomers of up to six monomer units that are derived from the cellulose portion of the pretreated lignocellulosic feedstock. Examples of soluble sugars are glucose, cellobiose, cellodextrins, or mixtures thereof. Preferably, the soluble sugars are predominantly cellobiose and glucose. In a more preferred embodiment, the soluble sugars are predominantly glucose.

The enzymatic hydrolysis process preferably converts about 80% to about 100% of the cellulose to soluble sugars, or any range therebetween. More preferably, the enzymatic hydrolysis process converts about 90% to about 100% of the cellulose to soluble sugars, or any range therebetween. In the most preferred embodiment, the enzymatic hydrolysis process converts about 98% to about 100% of the cellulose to soluble sugars, or any range therebetween.

The enzymatic hydrolysis using the cellulase mixture may be batch hydrolysis, continuous hydrolysis, or a combination thereof. The hydrolysis may be agitated, unmixed, or a combination thereof.

The enzymatic hydrolysis is preferably carried out at a temperature of about 45° C. to about 75° C., or any amount therebetween, and a pH of about 3.5 to about 7.5, or any amount therebetween. The initial concentration of cellulose in the hydrolysis reactor, prior to the start of hydrolysis, is preferably about 4% (w/w) to about 15% (w/w), or any amount therebetween. The combined dosage of all primary cellulase enzymes may be about 5 to about 45 mg protein per gram cellulose, or any amount therebetween. The hydrolysis may be carried out for a time period of about 12 hours to about 200 hours, or any amount therebetween. Preferably, the hydrolysis is carried out for a period of 15 hours to 100 hours. It should be appreciated that the reaction conditions are not meant to limit the invention in any manner and may be adjusted as desired by those of skill in the art.

The enzymatic hydrolysis is typically carried out in a hydrolysis reactor. The primary cellulase enzymes are added to the pretreated lignocellulosic feedstock (also referred to as the "substrate") prior to, during, or after the addition of the substrate to the hydrolysis reactor.

Preferably, the primary cellulases are produced in one or more submerged liquid culture fermentations and separated from the cells at the end of the fermentation. The cells may be separated from the cellulases by filtration, centrifugation, or other processes familiar to those skilled in the art. The cell-free cellulase-containing fraction may then be concentrated (for example, via ultrafiltration), preserved, and/or stabilized prior to use. Alternatively, the primary cellulases are not separated from the cells, but are added to the enzymatic hydrolysis with the cells.

The cellulase mixture may be an aqueous solution of protein in water, a slurry of protein in water, a solid powder or granule, or a gel. The blend comprising cellulase enzymes may include additives such as buffers, detergents, stabilizers, fillers, or other such additives familiar to those skilled in the art.

Preferably, the primary cellulases are expressed from fungal coding sequences. In this embodiment, the coding sequences would be from any fungal source. The terms "fungus," "fungi," "fungal," "*Ascomycotina*," "*Basidiomycotina*" and related terms (e.g. "ascomycete" and "basidiomycete") and are meant to include those organisms defined as such in *The Fungi: An Advanced Treatise* (G C Ainsworth, F K Sparrow, A S Sussman, eds.; Academic Press 1973).

Any source of cellulase enzymes may be used in the practice of the invention. The coding sequences of the cellulases of the invention are preferably from *Ascomycotina* or *Basidomycotina*. For example, the coding sequences are from the genera selected from *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomiun* ssp., *Fusarium* ssp., *Penicillium* ssp., *Magnaporthe* ssp., and *Phanerochaete* ssp. Preferably, the coding sequences for the primary cellulases are from *Trichoderma reesei*.

The primary cellulases of the invention may be cloned and expressed in a micro-organism known to those of skill in the art as an expression host, such as a bacterium or a fungus. Preferably, the micro-organism is a fungus. The genetic construct may be introduced into the host microbe by any number of methods known by one skilled in the art of microbial transformation, including but not limited to, treatment of cells with $CaCl_2$, electroporation, biolistic bombardment, PEG-mediated fusion of protoplasts (e.g. White et al., WO 2005/093072, which is incorporated herein by reference).

All of the primary cellulases may be expressed from one strain of an organism. Alternatively, the primary cellulases may be expressed individually or in sub-groups from different strains of different organisms. It is also contemplated that the primary cellulases may be expressed individually or in sub-groups from different strains of a single organism, such as from different strains of *Trichoderma reesei*. Preferably, all of the cellulases are expressed from a single strain of *Trichoderma reesei*.

The primary cellulases are preferably part of a total cellulase system produced by the expression organism(s). In one embodiment, the primary cellulases are the only cellulase enzymes of the cellulase system. In another embodiment, the primary cellulases are part of a cellulase system that includes β-glucosidase.

The primary cellulases may be part of a total cellulase system that includes the secretome of *Trichoderma reesei*. By the term "secretome", it is meant all proteins secreted extracellularly into the growth medium by a specific microorganism. In a preferred embodiment, the primary cellulases are part of a total cellulase system that includes the BGL1 β-glucosidase of *Trichoderma reesei* and the secretome of *Trichoderma reesei*.

The soluble sugars produced by the enzymatic hydrolysis may be fermented by microbes. The fermentation products can include any desired products that generate value to the fermentation plant. The preferred fermentation products are ethanol, butanol and lactic acid, all of which have large markets and are made efficiently by many microbes. For ethanol production, fermentation can be carried out by one or more than one microbe that is able to ferment the sugars to ethanol. For example, the fermentation may be carried out by recombinant *Saccharomyces* yeast that has been engineered to ferment glucose, mannose, galactose and xylose to ethanol, or glucose, mannose, galactose, xylose, and arabinose to ethanol. Recombinant yeasts that can ferment xylose to ethanol are described in U.S. Pat. No. 5,789,210 (which is herein incorporated by reference). The yeast produces a fermentation broth comprising ethanol in an aqueous solution. For lactic acid production, the fermentation can be carried out by a microbe that ferments the sugars to lactic acid.

In one embodiment of the invention, the cellulase enzyme mixture are produced by expressing the primary cellulases from a microorganism at acidic pH values. Preferably, the pH values are between about 2 and about 5. For example, the pH of the fermentation may be about 2.0, 2.2, 2.4, 2.6, 2.8, 3.0, 3.2, 3.4, 3.6, 3.8, 4.0, 4.2, 4.4, 4.6, 4.8 or 5.0.

The enzyme mixtures of the invention are of very different composition than those described in the prior art for cellulose hydrolysis. The primary cellulase mixtures of the invention are compositions significantly different from a "Benchmark Blend", a CBH1, CBH2, EG1 and EG2 composition of 57%, 29%, 7%, 7%, respectively. The best mixtures are mapped on FIGS. 3A, 3B and 3C and the Benchmark Blend is indicated where it occurs in the blend space mapped on FIG. 3D. The three dimensional representations of the component blend space described by these zones are shown in FIG. 4. The enzyme mixtures of the present invention have higher activity than those described in the prior art. Zones 1, 2 and 3 of the figures display activity increases of 10% or more when compared to the Benchmark Blend. Zones 2 and 3 exhibit activity increases of 13% or more when compared to the Benchmark Blend. Mixtures defined by Zone 3 exhibit increases of 16% more relative to the Benchmark Blend.

The irregular shape of the mapped Zones of FIGS. 3A, 3B and 3C was not foreseen and indicates steep activity dines within the entire blend space. The cellulase mixture of the invention defines a space that is more complicated than could be accounted for by prior work using model substrates or enzyme mixtures of less than four primary cellulases.

Past efforts to optimize blends typically employed ternary blends plotted on a triangular plot (c.f. Baker et al., 1998). Such efforts fall on the corners, edges or surfaces of the space, and thus are distant from the actual optimum.

The present invention will be further illustrated in the following examples.

EXAMPLES

Example 1

Purification of the Primary Cellulases CBH1, CBH2, EG1 and EG2 from *Trichoderma reesei* Cellulase A strain of *Trichoderma reesei* was grown in submerged liquid fermentation under conditions that induce cellulase production as known to those skilled in the art. The crude mixture of *Trichoderma* proteins were secreted by the cells into the fermentation broth. The fungal cells were removed from the fermentation broth by filtration across a glass microfiber filter containing a Harborlite filter bed. The primary cellulases (CBH1, CBH2, EG1, EG2) were separated from the crude filtrate by anion exchange chromatography using a DEAE-Sepharose column as described by Bhikhabhai et al. (1984). This step isolates EG1 and EG2. CBH1 and CBH2 were then further purified by p-aminophenyl-1-thio-β-D-cellobioside affinity chromatography as reported by Piyachomkwan et al. (1997, 1998). Purified cellulase components were concentrated and buffer exchanged into 50 mM sodium citrate, pH 5.0 using a stirred ultrafiltration cell (Amicon) and a 10 kDa NMWL polyethersulfone membrane.

Example 2

Measuring the Concentration and Purity of the Primary Cellulases

Protein concentrations were determined chemically using the method of Bradford et al. (1976). Samples of each purified protein were separated by SDS-PAGE and visualized post-electrophoretically by Commassie Blue staining as shown in FIG. 1, panel A. For each purified component, the staining intensity of each band was quantified by scanning densitometry using a Chemigenius2 (Syngene) imaging system. Relative purity was calculated by dividing the band intensity for each component by the total staining intensity measured for all bands in the same lane on the gel. EG2 lacking a carbohydrate-binding module was present in trace quantities but was not considered a contaminant in this enzyme preparation. The relative purity of CBH1 and CBH2 was >95% while that for EG1 and EG2 was >90%.

To demonstrate that each component preparation was devoid of contaminating primary cellulases, purified CBH1, CBH2, EG1, EG2 were analyzed by Western blotting using component-specific polyclonal antisera from rabbit (FIG. 1, panel B). Proteins were separated by 10% SDS-PAGE and transferred to a polyvinylidene fluoride (PVDF) membrane at 100 V for 1 hr using a Mini Trans-Blot® Cell from BioRad. Western blotting was performed using the method of Birkett et al. The component-specific polyclonal antisera were generated using synthetic peptides, the sequences of which were based on the primary amino acid sequence of CBH1, CBH2, EG1 or EG2 from *Trichoderma reesei*, as known to those skilled in the art.

These examples demonstrated that the purification methods used yielded substantially pure CBH1, CBH2, EG1 and EG2. This also demonstrated the specificity of these antisera for each of these primary cellulase components.

Example 3

Determining the Relative Concentrations of CBH1, CBH2, EG1 and EG2 in *Trichoderma* Cellulase The relative concentrations of CBH1, CBH2, EG1 and EG2 in cellulase from *Trichoderma reesei* were determined by ELISA.

Cellulase and purified component standards were diluted 1-100 μg/mL in phosphate-buffered saline, pH 7.2 (PBS) and incubated overnight at 4° C. in microtitre plates (Costar EIA—high binding). These plates were washed with PBS containing 0.1% Tween 20 (PBS/Tween) and then incubated in PBS containing 1% bovine serum albumin (PBS/BSA) for 1 hr at room temperature. Blocked microtitre wells were washed with PBS/Tween. Rabbit polyclonal antisera specific for CBH1, CBH2, EG1 and EG2 were diluted in PBS/BSA, added to separate microtitre plates and incubated for 2 hr at room temperature. Plates were washed and incubated with a goat anti-rabbit antibody coupled to horseradish peroxidase for 1 hr at room temperature. After washing, tetramethylbenzidine was added to each plate and incubated for 1 hr at room temperature.

The absorbance at 360 nm was measured in each well and converted into protein concentration using the CBH1, CBH2, EG1 and EG2 standards developed in Example 2. The relative concentration of each component was calculated by dividing these protein concentrations by the total concentration of CBH1, CBH2, EG1 and EG2.

Figure 2:
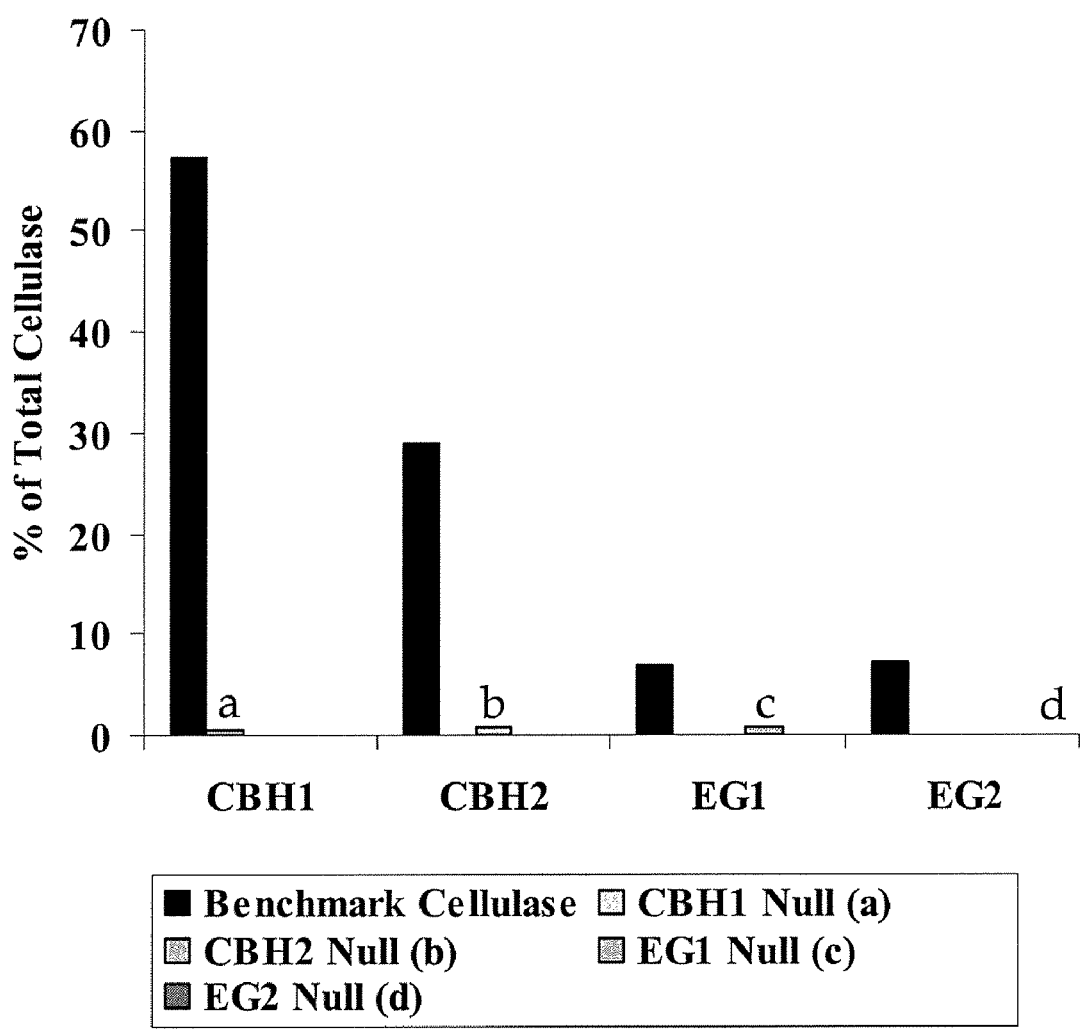
FIG. 2 is a column graph depicting the results of the ELISA analyses. The solid black columns illustrate the percentage composition of CBH1, CBH2, EG1 and EG2 in the commercial *Trichoderma* cellulase. The remaining columns demonstrate the level of specificity of each ELISA. The percent composition of: CBH1 in cellulase devoid of CBH1 (a), CBH2 in a cellulase devoid of CBH2 (b), EG1 in a cellulase devoid of EG1 (c) and EG2 in a cellulase devoid of EG2 (d) is shown.

The relative CBH1, CBH2, EG1 and EG2 composition in the *Trichoderma* cellulase was 57%:29%:7%:7%, respectively (FIG. 2). This will be referred to herein as our Benchmark Blend. This Blend is from a commercial *Trichoderma* cellulase product and is mapped as follows.

The concentration of CBHs relative to the entire set of primary cellulases (% CBH) is 57%+29%=86%. This places the set on FIG. 3D, which is 85% to 95% CBHs. The other figures are FIG. 3A, with % CBH=55% to 65%, FIG. 3B, with % CBH=65% to 75% and FIG. 3C with % CBH=75% to 85%.

The concentration of CBH2 relative to all CBH ($f_{C2}$) is 29%/(57%+29%)=0.337.

The concentration of EG2 relative to all primary EG ($f_{E2}$) is 7%/(7%+7%)=0.5.

Cellulase from strains of *Trichoderma* that do not secrete CBH1 (CBH1 null), CBH2 (CBH2 null), EG1 (EG1 null) or EG2 (EG2 null) were also analyzed to demonstrate that each ELISA detected CBH1, CBH2, EG1 or EG2 specifically (FIG. 2).

Example 4

Measuring the Cellulose Hydrolysis Activity of Primary Cellulase Blends on a Pretreated Lignocellulosic Feedstock A blend of primary cellulases with our Benchmark CBH1, CBH2, EG1 and EG2 ratios from Example 3 was compared to the mixtures with different compositions. These mixtures of primary cellulases were tested in a 0.25 mL mixed cellulose hydrolysis assay. Cellulase mixtures were diluted in citrate buffer containing 0.5% sodium benzoate, complemented with a β-glucosidase preparation from *Aspergillis niger* and incubated with acid pretreated wheat straw. The pretreatment was carried out as per Foody, U.S. Pat. No. 4,461,648. Incubation was at 50° C. for 24 hr and the target cellulose conversion level was greater than 70%. The enzyme activity was calculated by determining the amount of enzyme required to reach the target cellulose conversion level and normalizing to that required for the Benchmark cellulase blend.

The uncertainty of the normalized values is on the order of ±0.04, indicating that a value 10% above that observed for the benchmark (i.e., a normalized value of 1.10) can be said to be significantly greater than the benchmark. A weighted average across three-dimensional blend space (space with the dimensions $f_{C2}$, $f_{E2}$, and % CBH) was applied to smooth the activity data. The normalized activity data for a given point (the coordinates of this point are $f_{C2}$=x, $f_{E2}$=y, % CBH=z) was averaged with its six most closely neighbouring points with the following coordinates: x+0.1, y, z; x−0.1, y, z; x, y+0.1, z; x, y−0.1, z; x, y, z+10%; and x, y, z−10%. The point in question was given a weighting w=1.00 and the six neighbouring points were each given a weighting of w=0.15 in the following formula for the weighted average ($x_w$): $x_w = \Sigma w_i x_i / \Sigma w_i$ where the subscript i denotes a counting variable to sum over all 7 points described above and $x_i$ and $w_i$ indicate the normalized activity and weighting of the $i^{th}$ point respectively.

To represent these results graphically, the enzyme activity is shown on FIG. 3A, 3B, 3C, or 3D as described in Example 3 and illustrated in Table 1.

TABLE 1

Normalized glucose production by primary cellulase mixtures

| Mixture | % CBH1 | % CBH2 | % EG1 | % EG2 | % CBH* | FIG. | $f_{C2}$** | $f_{E2}$*** | Activity |
|---|---|---|---|---|---|---|---|---|---|
| Benchmark Blend | 57% | 29% | 7% | 7% | 86% | 1D | 0.333 | 0.500 | 1.00 |
| 1 | 36% | 23% | 37% | 4% | 59% | 1A | 0.396 | 0.087 | 1.08 |
| 2 | 36% | 23% | 33% | 8% | 59% | 1A | 0.396 | 0.187 | 1.11 |
| 3 | 36% | 23% | 29% | 12% | 59% | 1A | 0.396 | 0.287 | 1.10 |
| 4 | 30% | 29% | 37% | 4% | 59% | 1A | 0.496 | 0.087 | 1.09 |
| 5 | 30% | 29% | 33% | 8% | 59% | 1A | 0.496 | 0.187 | 1.11 |
| 6 | 30% | 29% | 29% | 12% | 59% | 1A | 0.496 | 0.287 | 1.09 |
| 7 | 30% | 29% | 25% | 16% | 59% | 1A | 0.496 | 0.387 | 1.11 |
| 8 | 24% | 35% | 37% | 4% | 59% | 1A | 0.596 | 0.087 | 1.06 |
| 9 | 24% | 35% | 33% | 8% | 59% | 1A | 0.596 | 0.187 | 1.06 |
| 10 | 24% | 35% | 29% | 12% | 59% | 1A | 0.596 | 0.287 | 1.04 |
| 11 | 24% | 35% | 25% | 16% | 59% | 1A | 0.596 | 0.387 | 1.06 |
| 12 | 62% | 7% | 28% | 3% | 69% | 1B | 0.096 | 0.087 | 0.90 |
| 13 | 62% | 7% | 25% | 6% | 69% | 1B | 0.096 | 0.187 | 0.91 |
| 14 | 62% | 7% | 22% | 9% | 69% | 1B | 0.096 | 0.287 | 0.91 |
| 15 | 56% | 14% | 28% | 3% | 69% | 1B | 0.196 | 0.087 | 1.05 |
| 16 | 56% | 14% | 25% | 6% | 69% | 1B | 0.196 | 0.187 | 1.08 |
| 17 | 56% | 14% | 22% | 9% | 69% | 1B | 0.196 | 0.287 | 1.08 |
| 18 | 56% | 14% | 19% | 12% | 69% | 1B | 0.196 | 0.387 | 1.02 |
| 19 | 49% | 20% | 28% | 3% | 69% | 1B | 0.296 | 0.087 | 1.15 |
| 20 | 49% | 20% | 25% | 6% | 69% | 1B | 0.296 | 0.187 | 1.14 |
| 21 | 49% | 20% | 22% | 9% | 69% | 1B | 0.296 | 0.287 | 1.13 |
| 22 | 49% | 20% | 19% | 12% | 69% | 1B | 0.296 | 0.387 | 1.08 |
| 23 | 49% | 20% | 16% | 15% | 69% | 1B | 0.296 | 0.487 | 1.08 |
| 24 | 49% | 20% | 13% | 18% | 69% | 1B | 0.296 | 0.587 | 1.06 |
| 25 | 42% | 27% | 28% | 3% | 69% | 1B | 0.396 | 0.087 | 1.14 |
| 26 | 42% | 27% | 25% | 6% | 69% | 1B | 0.396 | 0.187 | 1.14 |
| 27 | 42% | 27% | 22% | 9% | 69% | 1B | 0.396 | 0.287 | 1.13 |
| 28 | 42% | 27% | 19% | 12% | 69% | 1B | 0.396 | 0.387 | 1.13 |
| 29 | 42% | 27% | 16% | 15% | 69% | 1B | 0.396 | 0.487 | 1.14 |
| 30 | 42% | 27% | 13% | 18% | 69% | 1B | 0.396 | 0.587 | 1.06 |
| 31 | 42% | 27% | 10% | 21% | 69% | 1B | 0.396 | 0.687 | 1.05 |
| 32 | 35% | 34% | 28% | 3% | 69% | 1B | 0.496 | 0.087 | 1.11 |
| 33 | 35% | 34% | 25% | 6% | 69% | 1B | 0.496 | 0.187 | 1.16 |
| 34 | 35% | 34% | 22% | 9% | 69% | 1B | 0.496 | 0.287 | 1.17 |

TABLE 1-continued

Normalized glucose production by primary cellulase mixtures

| Mixture | % CBH1 | % CBH2 | % EG1 | % EG2 | % CBH* | FIG. | $f_{C2}$** | $f_{E2}$*** | Activity |
|---|---|---|---|---|---|---|---|---|---|
| 35 | 35% | 34% | 19% | 12% | 69% | 1B | 0.496 | 0.387 | 1.17 |
| 36 | 35% | 34% | 16% | 15% | 69% | 1B | 0.496 | 0.487 | 1.18 |
| 37 | 35% | 34% | 13% | 18% | 69% | 1B | 0.496 | 0.587 | 1.12 |
| 38 | 35% | 34% | 10% | 21% | 69% | 1B | 0.496 | 0.687 | 1.07 |
| 39 | 28% | 41% | 28% | 3% | 69% | 1B | 0.596 | 0.087 | 1.11 |
| 40 | 28% | 41% | 25% | 6% | 69% | 1B | 0.596 | 0.187 | 1.14 |
| 41 | 28% | 41% | 22% | 9% | 69% | 1B | 0.596 | 0.287 | 1.14 |
| 42 | 28% | 41% | 19% | 12% | 69% | 1B | 0.596 | 0.387 | 1.16 |
| 43 | 28% | 41% | 16% | 15% | 69% | 1B | 0.596 | 0.487 | 1.15 |
| 44 | 28% | 41% | 13% | 18% | 69% | 1B | 0.596 | 0.587 | 1.11 |
| 45 | 28% | 41% | 10% | 21% | 69% | 1B | 0.596 | 0.687 | 1.07 |
| 46 | 21% | 48% | 28% | 3% | 69% | 1B | 0.696 | 0.087 | 1.07 |
| 47 | 21% | 48% | 25% | 6% | 69% | 1B | 0.696 | 0.187 | 1.11 |
| 48 | 21% | 48% | 22% | 9% | 69% | 1B | 0.696 | 0.287 | 1.10 |
| 49 | 21% | 48% | 19% | 12% | 69% | 1B | 0.696 | 0.387 | 1.10 |
| 50 | 21% | 48% | 16% | 15% | 69% | 1B | 0.696 | 0.487 | 1.10 |
| 51 | 14% | 55% | 28% | 3% | 69% | 1B | 0.796 | 0.087 | 1.00 |
| 52 | 14% | 55% | 25% | 6% | 69% | 1B | 0.796 | 0.187 | 1.02 |
| 53 | 14% | 55% | 22% | 9% | 69% | 1B | 0.796 | 0.287 | 1.00 |
| 54 | 14% | 55% | 19% | 12% | 69% | 1B | 0.796 | 0.387 | 1.00 |
| 55 | 71% | 8% | 19% | 2% | 79% | 1C | 0.096 | 0.087 | 0.90 |
| 56 | 71% | 8% | 17% | 4% | 79% | 1C | 0.096 | 0.187 | 0.89 |
| 57 | 64% | 15% | 19% | 2% | 79% | 1C | 0.196 | 0.087 | 1.00 |
| 58 | 64% | 15% | 17% | 4% | 79% | 1C | 0.196 | 0.187 | 1.05 |
| 59 | 64% | 15% | 15% | 6% | 79% | 1C | 0.196 | 0.287 | 1.04 |
| 60 | 56% | 23% | 19% | 2% | 79% | 1C | 0.296 | 0.087 | 1.06 |
| 61 | 56% | 23% | 17% | 4% | 79% | 1C | 0.296 | 0.187 | 1.08 |
| 62 | 56% | 23% | 15% | 6% | 79% | 1C | 0.296 | 0.287 | 0.97 |
| 63 | 56% | 23% | 13% | 8% | 79% | 1C | 0.296 | 0.387 | 0.92 |
| 64 | 56% | 23% | 11% | 10% | 79% | 1C | 0.296 | 0.487 | 0.90 |
| 65 | 56% | 23% | 9% | 12% | 79% | 1C | 0.296 | 0.587 | 0.88 |
| 66 | 48% | 31% | 19% | 2% | 79% | 1C | 0.396 | 0.087 | 1.10 |
| 67 | 48% | 31% | 17% | 4% | 79% | 1C | 0.396 | 0.187 | 1.13 |
| 68 | 48% | 31% | 15% | 6% | 79% | 1C | 0.396 | 0.287 | 1.08 |
| 69 | 48% | 31% | 13% | 8% | 79% | 1C | 0.396 | 0.387 | 1.03 |
| 70 | 48% | 31% | 11% | 10% | 79% | 1C | 0.396 | 0.487 | 1.01 |
| 71 | 48% | 31% | 9% | 12% | 79% | 1C | 0.396 | 0.587 | 0.92 |
| 72 | 40% | 39% | 19% | 2% | 79% | 1C | 0.496 | 0.087 | 1.09 |
| 73 | 40% | 39% | 17% | 4% | 79% | 1C | 0.496 | 0.187 | 1.16 |
| 74 | 40% | 39% | 15% | 6% | 79% | 1C | 0.496 | 0.287 | 1.15 |
| 75 | 40% | 39% | 13% | 8% | 79% | 1C | 0.496 | 0.387 | 1.13 |
| 76 | 40% | 39% | 11% | 10% | 79% | 1C | 0.496 | 0.487 | 1.14 |
| 77 | 40% | 39% | 9% | 12% | 79% | 1C | 0.496 | 0.587 | 1.10 |
| 78 | 32% | 47% | 19% | 2% | 79% | 1C | 0.596 | 0.087 | 1.08 |
| 79 | 32% | 47% | 17% | 4% | 79% | 1C | 0.596 | 0.187 | 1.15 |
| 80 | 32% | 47% | 15% | 6% | 79% | 1C | 0.596 | 0.287 | 1.10 |
| 81 | 32% | 47% | 13% | 8% | 79% | 1C | 0.596 | 0.387 | 1.04 |
| 82 | 32% | 47% | 11% | 10% | 79% | 1C | 0.596 | 0.487 | 1.03 |
| 83 | 32% | 47% | 9% | 12% | 79% | 1C | 0.596 | 0.587 | 1.01 |
| 84 | 24% | 55% | 19% | 2% | 79% | 1C | 0.696 | 0.087 | 1.00 |
| 85 | 24% | 55% | 17% | 4% | 79% | 1C | 0.696 | 0.187 | 1.06 |
| 86 | 24% | 55% | 15% | 6% | 79% | 1C | 0.696 | 0.287 | 1.06 |
| 87 | 16% | 63% | 19% | 2% | 79% | 1C | 0.796 | 0.087 | 0.95 |
| 88 | 16% | 63% | 17% | 4% | 79% | 1C | 0.796 | 0.187 | 0.94 |
| 89 | 16% | 63% | 15% | 6% | 79% | 1C | 0.796 | 0.287 | 0.98 |
| 90 | 63% | 26% | 10% | 1% | 89% | 1D | 0.296 | 0.087 | 0.92 |
| 91 | 63% | 26% | 9% | 2% | 89% | 1D | 0.296 | 0.187 | 0.96 |
| 92 | 63% | 26% | 8% | 3% | 89% | 1D | 0.296 | 0.287 | 0.92 |
| 93 | 54% | 35% | 10% | 1% | 89% | 1D | 0.396 | 0.087 | 0.96 |
| 94 | 54% | 35% | 9% | 2% | 89% | 1D | 0.396 | 0.187 | 1.06 |
| 95 | 54% | 35% | 8% | 3% | 89% | 1D | 0.396 | 0.287 | 1.00 |
| 96 | 45% | 44% | 10% | 1% | 89% | 1D | 0.496 | 0.087 | 1.02 |
| 97 | 45% | 44% | 9% | 2% | 89% | 1D | 0.496 | 0.187 | 1.07 |
| 98 | 45% | 44% | 8% | 3% | 89% | 1D | 0.496 | 0.287 | 1.05 |
| 99 | 45% | 44% | 7% | 4% | 89% | 1D | 0.496 | 0.387 | 0.97 |
| 100 | 36% | 53% | 10% | 1% | 89% | 1D | 0.596 | 0.087 | 1.07 |
| 101 | 36% | 53% | 9% | 2% | 89% | 1D | 0.596 | 0.187 | 1.08 |
| 102 | 36% | 53% | 8% | 3% | 89% | 1D | 0.596 | 0.287 | 0.98 |
| 103 | 36% | 53% | 7% | 4% | 89% | 1D | 0.596 | 0.387 | 0.93 |
| 104 | 27% | 62% | 10% | 1% | 89% | 1D | 0.696 | 0.087 | 0.86 |
| 105 | 27% | 62% | 9% | 2% | 89% | 1D | 0.696 | 0.187 | 0.90 |
| 106 | 27% | 62% | 8% | 3% | 89% | 1D | 0.696 | 0.287 | 0.91 |

*% CBH = % CBH1 + % CBH2
**$f_{C2}$ = CBH2/(CBH1 + CBH2)
***$f_{E2}$ = EG2/(EG1 + EG2)

Figure 3D:
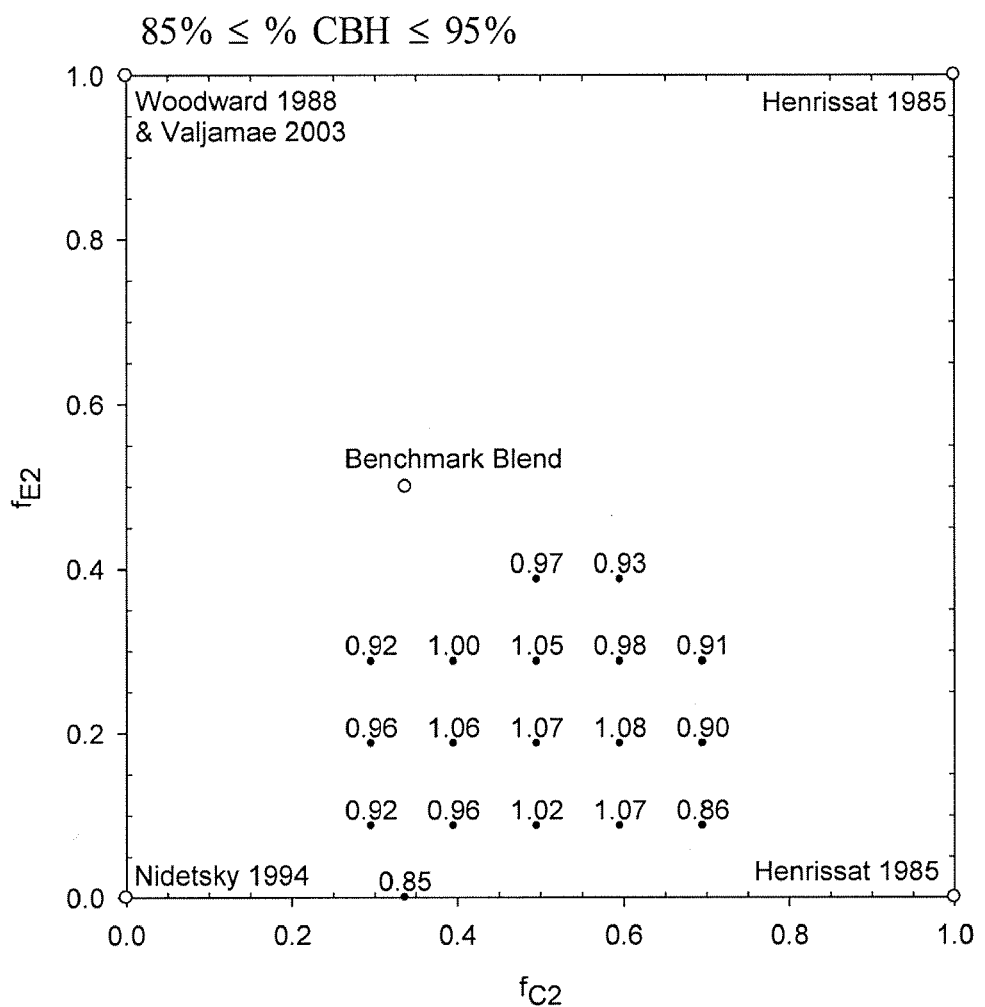
FIG. 3D shows the activities of mixtures in which the combined CBH1 and CBH2 content is greater than or equal to 85% and less than or equal to 95% of the total primary cellulases.

These plots are shown representing cellulase mixtures having fractional CBH contents (% CBH) within the following ranges: 55-65% (FIG. 3A), 65-75% (FIG. 3B), FIG. 3C), and 85-95% (FIG. 3D).

The shaded areas in FIGS. 3A, 3B and 3C represent the relative hydrolysis activities for mixtures with significantly higher activity than the Benchmark blend. The activity is 1.10-1.12 in Zone 1, which is 10% to 12% higher activity than the Benchmark Blend. The activity is 1.13-1.15 in Zone 2. This is 13% to 15% higher activity than the Benchmark Blend. The highest activity of 1.16-1.18 is in Zone 3, which is 16% to 18% higher than the Benchmark Blend. FIG. 3A, which encompasses 55% to 65% CBHs, does not have any mixtures with activity above 1.12 and therefore only includes values within Zone 1. FIG. 3D, which encompasses 85% to 95% CBHs, does not have any mixtures with activity above 1.10.

There are several interesting aspects to the results shown in FIGS. 3A, 3B, 3C and 3D. First, there are mixtures of primary cellulases identified with significantly higher activity than the Benchmark Blend, which itself represents the proportions of primary cellulases found in typical commercially available cellulase enzymes. This shows it is possible to produce cellulase mixtures that are >15% more potent than currently available blends. These blends differ significantly in composition from the Benchmark Blend.

A second point is the irregular shape of the mapped zones. These irregular shapes were not foreseen and indicate steep activity dines within the entire blend space. The experimental data defines a space that is more complicated than could be accounted for by prior work using model substrates or enzyme mixtures of less than four primary cellulases.

A third point is that the best mixtures are compositions significantly different from the prior art blends (see Example 5). Without being limited by theory, we feel it is necessary to use a pretreated lignocellulosic feedstock for the measurement of cellulase activity. Many prior art studies used pure cellulose model substrates.

Three dimensional representations of the component blend space comprised of these zones are shown in FIG. 4.

Example 5

Mapping Compositions of *Trichoderma* Cellulases

The relative compositions of ten *Trichoderma* cellulases for cellulose hydrolysis from scientific and patent literature were determined by dividing the reported protein concentration of CBH1, CBH2, EG1 and EG2 by that for the sum of these four components in each respective cellulase. These cellulases were then divided into groups based on their percent CBH as was done for the primary cellulase blends in Example 4. These cellulases were then plotted as a function of their $f_{C2}$ and $f_{E2}$ and subsequently compared to the zones associated with an improvement in cellulose hydrolysis activity relative to the benchmark component blend. *Trichoderma* cellulases in the literature with CBH<55% or CBH>95% were not included in this analysis.

All of the published compositions of primary cellulases lie well outside the zones that yield the highest cellulase activity.

TABLE 2

Mapping of known compositions onto FIG. 3

| Mixture | CBH1 (%) | CBH2 (%) | EG1 (%) | EG2 (%) | % CBH | FIG. | $f_{C2}$ | $f_{E2}$ |
|---|---|---|---|---|---|---|---|---|
| Baker et al. (1998) | 60 | 20 | 20 | 0 | 80 | 3C | 0.25 | 0 |
| Cytolase (in U.S. Pat. No. 5,525,507) | 50 | 14 | 12 | 9 | 75 | 3C | 0.22 | 0.43 |
| Henrissat et al. (1985) | 0 | 95 | 5 | 0 | 95 | 3D | 1 | 0 |
| Henrissat et al. (1985) | 0 | 95 | 0 | 5 | 95 | 3D | 1 | 1 |
| Jeoh et al. (2006) | 0 | 70 | 0 | 30 | 1 | 3B | 1 | 1 |
| Celloviridin (in Markov et al., 2005) | 50 | 30 | 10 | 10 | 80 | 3C | 0.38 | 0.5 |
| Nidetsky et al. (1994) | 88.6 | 0 | 11.4 | 0 | 88.6 | 3D | 0 | 0 |
| Valjamae et al. (2003) | 90.9 | 0 | 0 | 9.1 | 90.9 | 3D | 0 | 1 |
| Woodward et al. (1988) | 50 | 25 | 0 | 25 | 75 | 3B | 0.33 | 1 |
| Woodward et al. (1988) | 88 | 0 | 0 | 12 | 88 | 3D | 0 | 1 |

A *Trichoderma* cellulase lacking EG2 was also mapped onto FIG. 3D. This composition contained 61.3% CBH1, 31.2% CBH2, 7.5% EG1, and the $f_{C2}$ and $f_{E2}$ values were 0.337 and 0, respectively. This composition also lies outside the zones that yield the highest cellulase activity (see FIGS. 3B and 3C).

Example 6

Measuring the Hydrolysis Activity of Primary Cellulase Blends on Pretreated Lignocellulosic Feedstock Over an Extended Period A blend of primary cellulases with our Benchmark CBH1, CBH2, EG1 and EG2 ratios from Example 3 was compared to an improved blend with a 15% activity improvement in Example 4 in an extended hydrolysis. The improved blend was composed of 32% Cel7A, 47% Cel6A, 17% Cel7B and 4% Cel5A. Both blends were dosed at 18 mg enzyme per g of cellulose and further supplemented with a β-glucosidase preparation from *Aspergillus niger* at 100 IU/g cellulose.

Figure 5:
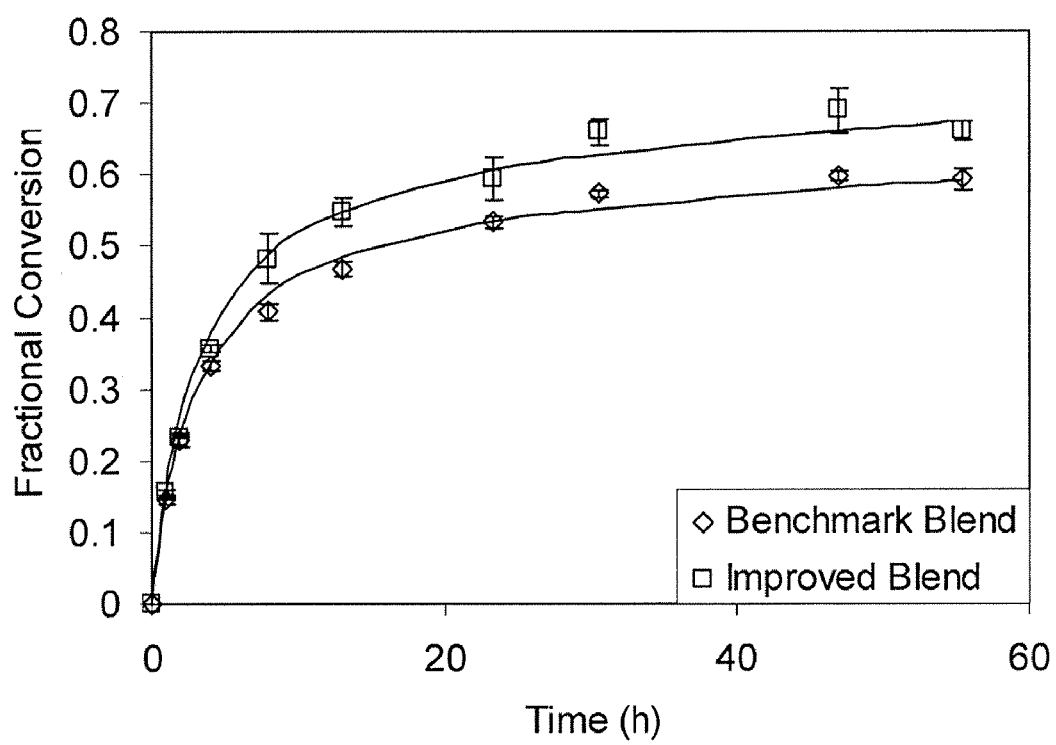
FIG. 5 is a plot showing the conversion of pretreated lignocellulosic substrate by the benchmark blend, which is a blend composed of primary cellulases in the relative proportions observed in a wild-type cellulase, and a representative improved blend.

The blends were incubated with 25 g/L cellulose in 50 mM citrate, pH 5.0, containing 0.5% sodium benzoate and 0.01% Triton X-100 at 50° C. for 56 hours with continuous shaking at 200 rpm. Aliquots of 0.5 mL were taken at the time points indicated in FIG. 5 and the glucose concentration in the soluble portion was assayed and converted into a fractional conversion. The conversion data were then fit with a rectangular hyperbola with an additional linear term using minimization of the sum of squared residuals of fit. The equation was of the following form: conversion=(max*time)/(halfmax+time)+c*time. Both sets of data were fit globally with unique max and halfmax values and a shared value of the variable c. Standard errors of the max conversion values were calculated using a model comparison approach (Motulsky and Christopolous, 2003). A t-test was used to compare the max conversion values for the benchmark and optimized blends (supra).

The max conversion value for the optimized blend was 0.69, an increase over the max conversion of 0.59 of the benchmark blend. This represents a significant increase ($P<0.05$) of 16%. The conversion of these blends will be higher in the presence of additional components of the cellulase apart from the four considered here.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

Baker, J., et al., "Hydrolysis of cellulose using ternary mixtures of purified cellulases", Applied Biochemistry and Biotechnology, 70-72:395-403, (1998).

Barr, B., et al., "Identification of two functionally different classes of exocellulases", Biochemistry, 35:586-592, (1996).

Berghem, L. and Pettersson, L., "The mechanism of enzymatic cellulose degradation. Purification of a cellulolytic enzyme from *Trichoderma viride* active on highly ordered cellulose.", European Journal of Biochemistry, 37:21-30, (1973).

Bhikhabhai, R., et al., "Isolation of Cellulolytic Enzymes from *Trichoderma reesei* QM 9414", Journal of Applied Biochemistry, 6:336-345 (1984).

Birkett, C. R., et al., "Use of monoclonal antibodies to analyze the expression of a multi-tubulin family", FEBS Letters, 187(2):211-218, (1985).

Boisset, C., et al., "Optimized mixtures of recombinant *Humicola insolens* cellulases for the biodegradation of crystalline cellulose", Biotechnology and Bioengineering, 72:339-345, (2001).

Bradford, M. M., et al., "A rapid and sensitive method for quantitation of microgram quantities of protein utilizing the principle of protein-dye binding", Analytical Biochemistry, 72:248-254, (1976).

Enari, T. M. and Niku-Paavola, M. L., "Assays for Cellulolytic Enzymes: Methods for Measuring Cellulase Activities", In J. N. Abelson and M. I. Simon (Ed/s.), Methods in Enzymology, 117-126, San Diego, Calif.: Academic Press, Inc., (1988).

Henrissat, B., et al., "Synergism of cellulases from *Trichoderma reesei* in the degradation of cellulose", Bio/Technology, 3:722-726, (1985).

Houghton, J., et al., "Breaking the Biological Barriers to Cellulosic Ethanol", U.S. Department of Energy Office of Science and Office of Energy Efficiency and Renewable Energy, DOE/SC-0095, (2006).

Hui, J., et al., "Characterization of cellobiohydrolase I (Cel7A) glycoforms from extracts of *Trichoderma reesei* using capillary isoelectric focusing and electrospray mass spectrometry", Journal of Chromatography B, 752:349-368, (2001).

Irwin, D., et al., "Activity studies of eight purified cellulases: specificity, synergism, and binding domain effects", Biotechnology and Bioengineering, 42:1002-1013, (1993).

Kim et al., "Factorial optimization of a six-cellulase mixture", Biotechnology and Bioengineering, 58:494-501, (1998).

Kubicek, C., "The cellulase proteins of *Trichoderma reesei*: Structure, multiplicity, mode of action and regulation of formation", Advances in Biochemical Engineering/Biotechnology, 45:2-22, (1992).

Motulsky, H, and Christopolous, A., "Fitting models to biological data using linear and nonlinear regression: A practical guide to curve fitting." Oxford University Press, New York, (2004).

Nidetsky, B., et al., "Cellulose hydrolysis by the cellulases from *Trichoderma reesei*: a new model for synergistic interaction.", Biochemical Journal, 298:705-710, (1994).

Öhgren, K., et al., "Optimization of Steam Pretreatment of $SO_2$-Impregnated Corn Stover for Fuel Ethanol Production", Applied Biochemistry and Biotechnology, 121-124: 1055-1067, (2005)

Piyachomkwan, K., et al., "p-Aminophenyl 1-thio-β-D-cellobioside: synthesis and application in affinity chromatography of exo-type cellulases", Carbohydrate Research, 303:255-259, (1997).

Piyachomkwan, K., et al., "Aryl Thioglycoside-Based Affinity Purification of Exo-Acting Cellulases", Analytical Biochemistry, 255:223-235, (1998).

Sheehan, J. and Himmel, M., "Enzymes, Energy, and the Environment: A Strategic Perspective on the U.S. Department of Energy's Research and Development Activities for Bioethanol", Biotechnology Progress, 15:817-827, (1999).

Tolan, J., "Iogen's process for producing ethanol from cellulosic biomass", Clean Technologies and Environmental Policy, 3:339-345, (2002).

Walker, L., et al., "Engineering cellulase mixtures by varying the mole fraction of *Thermonospora fusca* E5 and E3, *Trichoderma reesei* CBHI and *Caldocellum saccharolyticum* β-glucosidase", Biotechnology and Bioengineering, 42:1019-1028, (1993).

Weil, J. et al., "Preteatment of yellow poplar sawdust by pressure cooking in water", Applied Biochemistry and Biotechnology, 68(1-2):21-40 (1997).

Wood, T. and McCrae, S., "The cellulase of *Trichoderma koningii*. Purification and properties of some endoglucanase components with special reference to their action on cellulose when acting alone and in synergism with the cellobiohydrolase", Biochemical Journal, 171:61-72, (1972).

Wood, T. and McCrae, S., "Synergism between enzymes involved in the solubilization of native cellulose", Advances in Chemistry Series, 181:181-209, (1979).

Wood, T., et al., "The mechanism of fungal cellulase action: Synergism between enzyme components of *Penicillium pinophilum* cellulase in solubilizing hydrogen bond-ordered cellulose", Biochemical Journal, 260:37-43.

Woodward, J., et al., "The role of cellulase concentration in determining the degree of synergism in the hydrolysis of microcrystalline cellulose", Biochemical Journal, 255:895-899, (1988).

Zhang, S., et al., "Substrate heterogeneity causes the nonlinear kinetics of insoluble cellulose hydrolysis", Biotechnology and Bioengineering, 66:35-41, (1999).

All citations are incorporated herein by reference.

The invention claimed is:

1. A cellulase enzyme mixture comprising a primary cellulase mixture of CBH1 and CBH2 cellobiohydrolases and EG1 and EG2 endoglucanases, said CBH1 and CBH2 cellobiohydrolases being present at greater than or equal to 55% and less than 65% of the primary cellulase mixture, said CBH2 being present at a fraction relative to CBH1 and CBH2 cellobiohydrolases as defined by $f_{C2}$ and said EG2 being present at a fraction relative to the EG1 and EG2 endoglucanases as defined by $f_{E2}$, wherein said $f_{C2}$ is greater than or equal to 0.35 and less than 0.55, and
 (i) when said $f_{C2}$ value is greater than or equal to 0.35 and less than 0.45, said $f_{E2}$ value is greater than or equal to 0.15 and less than 0.35; and
 (ii) when said $f_{C2}$ value is greater than or equal to 0.45 and less than 0.55, said $f_{E2}$ value is greater than or equal to 0.15 and less than 0.25, or greater than or equal to 0.35 and less than 0.45.

2. The cellulase enzyme mixture of claim 1, wherein the cellulase enzyme mixture is produced by expressing the primary cellulases from *Trichoderma* at pH values between about 2 and about 5.

3. A cellulase enzyme mixture comprising a primary cellulase mixture of CBH1 and CBH2 cellobiohydrolases and EG1 and EG2 endoglucanases, said CBH1 and CBH2 cellobiohydrolases being present at greater than or equal to 65% and less than 75% of the primary cellulase mixture, said CBH2 being present at a fraction relative to CBH1 and CBH2 cellobiohydrolases as defined by $f_{C2}$ and said EG2 being present at a fraction relative to the EG1 and EG2 endoglucanases as defined by $f_{E2}$, wherein said $f_{C2}$ is greater than or equal to 0.25 and less than 0.75, and
 (i) when said $f_{C2}$ value is greater than or equal to 0.25 and less than 0.35, said $f_{E2}$ value is greater than or equal to 0.05 and less than 0.35;
 (ii) when said $f_{C2}$ value is greater than or equal to 0.35 and less than 0.45, said $f_{E2}$ value is greater than or equal to 0.05 and less than 0.55;
 (iii) when said $f_{C2}$ value is greater than or equal to 0.45 and less than 0.65, said $f_{E2}$ value is greater than or equal to 0.05 and less than 0.65; and
 (iv) when said $f_{C2}$ value is greater than or equal to 0.65 and less than 0.75, said $f_{E2}$ value is greater than or equal to 0.15 and less than 0.55.

4. The cellulase enzyme mixture of claim 3, wherein when said $f_{C2}$ value is greater than or equal to 0.45 and less than 0.65, said $f_{E2}$ value is greater than or equal to 0.15 and less than 0.55.

5. The cellulase enzyme mixture of claim 4, wherein when said $f_{C2}$ value is greater than or equal to 0.55 and less than 0.65, said $f_{E2}$ value is greater than or equal to 0.35 and less than 0.45.

6. The cellulase enzyme mixture of claim 4, wherein the cellulase enzyme mixture is produced by expressing the primary cellulases from *Trichoderma* at pH values between about 2 and about 5.

7. A cellulase enzyme mixture comprising a primary cellulase mixture of CBH1 and CBH2 cellobiohydrolases and EG1 and EG2 endoglucanases, said CBH1 and CBH2 cellobiohydrolases being present at greater than or equal to 75% and less than 85% of the primary cellulase mixture, said CBH2 being present at a fraction relative to CBH1 and CBH2 cellobiohydrolases as defined by $f_{C2}$ and said EG2 being present at a fraction relative to the EG1 and EG2 endoglucanases as defined by $f_{E2}$, wherein said $f_{C2}$ is greater than or equal to 0.35 and less than 0.65, and
 (i) when said $f_{C2}$ value is greater than or equal to 0.35 and less than 0.45, said $f_{E2}$ value is greater than or equal to 0.05 and less than 0.25;
 (ii) when said $f_{C2}$ value is greater than or equal to 0.45 and less than 0.55, said $f_{E2}$ value is greater than or equal to 0.15 and less than 0.65; and
 (iii) when said $f_{C2}$ value is greater than or equal to 0.55 and less than 0.65, said $f_{E2}$ value is greater than or equal to 0.15 and less than 0.35.

8. The cellulase enzyme mixture of claim 7, wherein
 (i) when said $f_{C2}$ values are greater than or equal to 0.35 and less than 0.45, said $f_{E2}$ value is greater than or equal to 0.15 and less than 0.25;
 (ii) when said $f_{C2}$ values are greater than or equal to 0.45 and less than 0.55, said $f_{E2}$ value is greater than or equal to 0.15 and less than 0.55; and
 (iii) when said $f_{C2}$ values are greater than or equal to 0.55 and less than 0.65, said $f_{E2}$ value is greater than or equal to 0.15 and less than 0.25.

9. The cellulase enzyme mixture of claim 8, wherein when said $f_{C2}$ values are greater than or equal to 0.45 and less than 0.55, said $f_{E2}$ values are greater than or equal to 0.15 and less than 0.25.

10. The cellulase enzyme mixture of claim 7, wherein the cellulase enzyme mixture is produced by expressing the primary cellulases from *Trichoderma* at pH values between about 2 and about 5.

11. The cellulase enzyme mixture of claim 3, wherein the cellulase enzyme mixture is produced by expressing the primary cellulases from *Trichoderma* at pH values between about 2 and about 5.

12. The cellulase enzyme mixture of claim 5, wherein the cellulase enzyme mixture is produced by expressing the primary cellulases from *Trichoderma* at pH values between about 2 and about 5.

13. A process for enzymatic hydrolysis of a pretreated lignocellulosic feedstock to soluble sugars, the process comprising adding the cellulase enzyme mixture as in any of claims 1-12 to the pretreated lignocellulosic feedstock and hydrolyzing under conditions suitable to convert the cellulose within said pretreated lingocellulosic feedstock to soluble sugars.

* * * * *

UNITED STATES PATENT AND TRADEMARK OFFICE
CERTIFICATE OF CORRECTION

| | | |
|---|---|---|
| PATENT NO. | : 8,017,373 B2 | |
| APPLICATION NO. | : 11/846653 | |
| DATED | : September 13, 2011 | |
| INVENTOR(S) | : Christopher Hill et al. | |

It is certified that error appears in the above-identified patent and that said Letters Patent is hereby corrected as shown below:

ON THE TITLE PAGE [56] REFERENCES CITED:

Other Publications, Under Walker, et al., "11-glucosidase"," should read --β-glucosidase",--.

COLUMN 5:

Line 36, "increases" should read --increase--.

COLUMN 7:

Line 19, "identify" should read --identity--; and
Line 22, "into" should read --by--.

COLUMN 13:

Line 7, "are" should read --is--.

COLUMN 24:

Line 56, "lingocellulosic" should be --lignocellulosic--.

Signed and Sealed this
Third Day of January, 2012

David J. Kappos
*Director of the United States Patent and Trademark Office*